US010492856B2

(12) United States Patent
Orczy-Timko

(10) Patent No.: US 10,492,856 B2
(45) Date of Patent: Dec. 3, 2019

(54) SURGICAL FLUID MANAGEMENT SYSTEM AND METHOD OF USE

(71) Applicant: Hermes Innovations, LLC, Cupertino, CA (US)

(72) Inventor: Benedek Orczy-Timko, Budapest (HU)

(73) Assignee: Hermes Innovations LLC, Cupertino, CA (US)

( * ) Notice: Subject to any disclaimer, the term of this patent is extended or adjusted under 35 U.S.C. 154(b) by 870 days.

(21) Appl. No.: 15/008,341

(22) Filed: Jan. 27, 2016

(65) Prior Publication Data

US 2016/0242844 A1 Aug. 25, 2016

Related U.S. Application Data

(60) Provisional application No. 62/107,953, filed on Jan. 26, 2015.

(51) Int. Cl.
*A61M 1/00* (2006.01)
*A61B 18/14* (2006.01)
(Continued)

(52) U.S. Cl.
CPC ..... *A61B 18/1492* (2013.01); *A61M 5/14212* (2013.01); *A61M 5/172* (2013.01);
(Continued)

(58) Field of Classification Search
CPC .......... A61M 39/24; A61M 2039/0009; A61M 5/14212; A61M 5/172; A61B 2018/00744; A61B 2018/00982; A61B 2218/001
See application file for complete search history.

(56) References Cited

U.S. PATENT DOCUMENTS 3,903,891 A 9/1975 Brayshaw
4,949,718 A 8/1990 Neuwirth et al.
(Continued)

FOREIGN PATENT DOCUMENTS

CN 101198288 A 6/2008
EP 1236440 A1 9/2002
(Continued)

OTHER PUBLICATIONS

European search report and search opinion dated Apr. 16, 2013 for EP Application No. 09822443.
(Continued)

*Primary Examiner* — Rebecca E Eisenberg
(74) *Attorney, Agent, or Firm* — Wilson Sonsini Goodrich & Rosati

(57) ABSTRACT

A fluid management system receives fluid from a fluid source and delivers the fluid to a medical probe having a first fluid infusion and aspiration circuit and a second fluid infusion and aspiration circuit. The system also transfers fluid from the medical probe to a collection container. A controller operates a first pump and valve assembly to selectively deliver fluid inflow from the fluid source to one of the first fluid infusion and the second fluid infusion and aspiration circuit. The controller further operates a second pump and valve assembly to selectively transfer fluid outflow to the collection container from one of the first fluid infusion and aspiration circuit of the medical probe and the second fluid infusion and aspiration circuit of the medical probe.

24 Claims, 15 Drawing Sheets

(51) Int. Cl.
    *A61M 39/24*      (2006.01)
    *A61M 5/142*      (2006.01)
    *A61M 5/172*      (2006.01)
    *A61B 18/00*      (2006.01)
    *A61M 39/00*      (2006.01)
    *A61B 90/00*      (2016.01)

(52) U.S. Cl.
    CPC ......... *A61M 39/24* (2013.01); *A61B 18/1477* (2013.01); *A61B 2018/00547* (2013.01); *A61B 2018/00577* (2013.01); *A61B 2018/00589* (2013.01); *A61B 2018/00601* (2013.01); *A61B 2018/00642* (2013.01); *A61B 2018/00744* (2013.01); *A61B 2018/00982* (2013.01); *A61B 2018/1472* (2013.01); *A61B 2090/378* (2016.02); *A61B 2218/002* (2013.01); *A61B 2218/007* (2013.01); *A61M 2039/0009* (2013.01)

(56) References Cited

U.S. PATENT DOCUMENTS

| | | |
|---|---|---|
| 4,979,948 A | 12/1990 | Geddes et al. |
| 5,045,056 A | 9/1991 | Behl |
| 5,078,717 A | 1/1992 | Parins et al. |
| 5,084,044 A | 1/1992 | Quint |
| 5,191,883 A | 3/1993 | Lennox et al. |
| 5,197,963 A | 3/1993 | Parins |
| 5,242,390 A | 9/1993 | Goldrath |
| 5,248,312 A | 9/1993 | Langberg |
| 5,277,201 A | 1/1994 | Stern |
| 5,282,799 A | 2/1994 | Rydell |
| 5,324,254 A | 6/1994 | Phillips |
| 5,344,435 A | 9/1994 | Turner et al. |
| 5,374,261 A | 12/1994 | Yoon |
| 5,401,272 A | 3/1995 | Perkins |
| 5,429,136 A | 7/1995 | Milo et al. |
| 5,441,498 A | 8/1995 | Perkins |
| 5,443,470 A | 8/1995 | Stern et al. |
| 5,496,314 A | 3/1996 | Eggers |
| 5,501,681 A | 3/1996 | Neuwirth et al. |
| 5,505,730 A | 4/1996 | Edwards |
| 5,558,672 A | 9/1996 | Edwards et al. |
| 5,562,703 A | 10/1996 | Desai |
| 5,562,720 A | 10/1996 | Stern et al. |
| 5,575,788 A | 11/1996 | Baker et al. |
| 5,584,872 A | 12/1996 | LaFontaine et al. |
| 5,647,848 A | 7/1997 | Jorgensen |
| 5,653,692 A | 8/1997 | Masterson et al. |
| 5,662,647 A | 9/1997 | Crow et al. |
| 5,672,174 A | 9/1997 | Gough et al. |
| 5,681,308 A | 10/1997 | Edwards et al. |
| 5,697,281 A | 12/1997 | Eggers et al. |
| 5,697,882 A | 12/1997 | Eggers et al. |
| 5,713,942 A | 2/1998 | Stern et al. |
| 5,769,846 A | 6/1998 | Edwards et al. |
| 5,769,880 A | 6/1998 | Truckai et al. |
| 5,800,493 A | 9/1998 | Stevens et al. |
| 5,810,802 A | 9/1998 | Panescu et al. |
| 5,827,273 A | 10/1998 | Edwards |
| 5,843,020 A | 12/1998 | Tu et al. |
| 5,846,239 A | 12/1998 | Swanson et al. |
| 5,860,974 A | 1/1999 | Abele |
| 5,876,340 A | 3/1999 | Tu et al. |
| 5,879,347 A | 3/1999 | Saadat |
| 5,891,094 A | 4/1999 | Masterson et al. |
| 5,891,134 A | 4/1999 | Goble et al. |
| 5,891,136 A | 4/1999 | McGee et al. |
| 5,902,251 A | 5/1999 | Vanhooydonk |
| 5,904,651 A | 5/1999 | Swanson et al. |
| 5,925,038 A | 7/1999 | Panescu et al. |
| 5,954,714 A | 9/1999 | Saadat et al. |
| 5,964,755 A | 10/1999 | Edwards |
| 5,976,129 A | 11/1999 | Desai |
| 5,980,515 A | 11/1999 | Tu |
| 5,997,534 A | 12/1999 | Tu et al. |
| 6,024,743 A | 2/2000 | Edwards |
| 6,026,331 A | 2/2000 | Feldberg et al. |
| 6,041,260 A | 3/2000 | Stern et al. |
| 6,053,909 A | 4/2000 | Shadduck |
| 6,057,689 A | 5/2000 | Saadat |
| 6,086,581 A | 7/2000 | Reynolds et al. |
| 6,113,597 A | 9/2000 | Eggers et al. |
| 6,139,570 A | 10/2000 | Saadat et al. |
| 6,146,378 A | 11/2000 | Mikus et al. |
| 6,149,620 A | 11/2000 | Baker et al. |
| 6,228,078 B1 | 5/2001 | Eggers et al. |
| 6,254,599 B1 | 7/2001 | Lesh et al. |
| 6,283,962 B1 | 9/2001 | Tu et al. |
| 6,296,639 B1 | 10/2001 | Truckai et al. |
| 6,302,904 B1 | 10/2001 | Wallstén et al. |
| 6,315,776 B1 | 11/2001 | Edwards et al. |
| 6,366,818 B1 | 4/2002 | Bolmsjo |
| 6,387,088 B1 | 5/2002 | Shattuck et al. |
| 6,395,012 B1 | 5/2002 | Yoon et al. |
| 6,409,722 B1 | 6/2002 | Hoey et al. |
| 6,416,508 B1 | 7/2002 | Eggers et al. |
| 6,416,511 B1 | 7/2002 | Lesh et al. |
| 6,443,947 B1 | 9/2002 | Marko et al. |
| 6,508,815 B1 | 1/2003 | Strul et al. |
| 6,551,310 B1 | 4/2003 | Ganz et al. |
| 6,589,237 B2 | 7/2003 | Woloszko et al. |
| 6,602,248 B1 | 8/2003 | Sharps et al. |
| 6,607,545 B2 | 8/2003 | Kammerer et al. |
| 6,622,731 B2 | 9/2003 | Daniel et al. |
| 6,635,054 B2 | 10/2003 | Fjield et al. |
| 6,635,055 B1 | 10/2003 | Cronin |
| 6,663,626 B2 | 12/2003 | Truckai et al. |
| 6,673,071 B2 | 1/2004 | Vandusseldorp et al. |
| 6,699,241 B2 | 3/2004 | Rappaport et al. |
| 6,726,684 B1 | 4/2004 | Woloszko et al. |
| 6,736,811 B2 | 5/2004 | Panescu et al. |
| 6,746,447 B2 | 6/2004 | Davison et al. |
| 6,758,847 B2 | 7/2004 | Maguire |
| 6,780,178 B2 | 8/2004 | Palanker et al. |
| 6,802,839 B2 | 10/2004 | Behl |
| 6,813,520 B2 | 11/2004 | Truckai et al. |
| 6,814,730 B2 | 11/2004 | Li |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,840,935 B2 | 1/2005 | Lee |
| 6,872,205 B2 | 3/2005 | Lesh et al. |
| 6,896,674 B1 | 5/2005 | Woloszko et al. |
| 6,905,497 B2 | 6/2005 | Truckai et al. |
| 6,923,805 B1 | 8/2005 | LaFontaine et al. |
| 6,929,642 B2 | 8/2005 | Xiao et al. |
| 6,949,096 B2 | 9/2005 | Davison et al. |
| 6,951,569 B2 | 10/2005 | Nohilly et al. |
| 6,954,977 B2 | 10/2005 | Maguire et al. |
| 6,960,203 B2 | 11/2005 | Xiao et al. |
| 7,074,217 B2 | 7/2006 | Strul et al. |
| 7,083,614 B2 | 8/2006 | Fjield et al. |
| 7,087,052 B2 | 8/2006 | Sampson et al. |
| 7,108,696 B2 | 9/2006 | Daniel et al. |
| 7,118,590 B1 | 10/2006 | Cronin |
| 7,175,734 B2 | 2/2007 | Stewart et al. |
| 7,179,255 B2 | 2/2007 | Lettice et al. |
| 7,186,234 B2 | 3/2007 | Dahla et al. |
| 7,192,430 B2 | 3/2007 | Truckai et al. |
| 7,238,185 B2 | 7/2007 | Palanker et al. |
| 7,270,658 B2 | 9/2007 | Woloszko et al. |
| 7,276,063 B2 | 10/2007 | Davison et al. |
| 7,278,994 B2 | 10/2007 | Goble |
| 7,294,126 B2 | 11/2007 | Sampson et al. |
| 7,297,143 B2 | 11/2007 | Woloszko et al. |
| 7,326,201 B2 | 2/2008 | Fjield et al. |
| 7,331,957 B2 | 2/2008 | Woloszko et al. |
| RE40,156 E | 3/2008 | Sharps et al. |
| 7,371,231 B2 | 5/2008 | Rioux et al. |
| 7,371,235 B2 | 5/2008 | Thompson et al. |
| 7,381,208 B2 | 6/2008 | Van Der Walt et al. |
| 7,387,628 B1 | 6/2008 | Behl et al. |

(56) References Cited

U.S. PATENT DOCUMENTS

| | | |
|---|---|---|
| 7,407,502 B2 | 8/2008 | Strul et al. |
| 7,419,500 B2 | 9/2008 | Marko et al. |
| 7,452,358 B2 | 11/2008 | Stern et al. |
| 7,462,178 B2 | 12/2008 | Woloszko et al. |
| 7,500,973 B2 | 3/2009 | Vancelette et al. |
| 7,512,445 B2 | 3/2009 | Truckai et al. |
| 7,530,979 B2 | 5/2009 | Ganz et al. |
| 7,549,987 B2 | 6/2009 | Shadduck |
| 7,556,628 B2 | 7/2009 | Utley et al. |
| 7,566,333 B2 | 7/2009 | Van Wyk et al. |
| 7,572,251 B1 | 8/2009 | Davison et al. |
| 7,604,633 B2 | 10/2009 | Truckai et al. |
| 7,625,368 B2 | 12/2009 | Schechter et al. |
| 7,674,259 B2 | 3/2010 | Shadduck |
| 7,678,106 B2 | 3/2010 | Lee |
| 7,708,733 B2 | 5/2010 | Sanders et al. |
| 7,717,909 B2 | 5/2010 | Strul et al. |
| 7,736,362 B2 | 6/2010 | Eberl et al. |
| 7,749,159 B2 | 7/2010 | Crowley et al. |
| 7,824,398 B2 | 11/2010 | Woloszko et al. |
| 7,824,405 B2 | 11/2010 | Woloszko et al. |
| 7,846,160 B2 | 12/2010 | Payne et al. |
| 7,879,034 B2 | 2/2011 | Woloszko et al. |
| 7,918,795 B2 | 4/2011 | Grossman |
| 7,985,188 B2 | 7/2011 | Felts et al. |
| 8,197,476 B2 | 6/2012 | Truckai |
| 8,197,477 B2 | 6/2012 | Truckai |
| 8,372,068 B2 | 2/2013 | Truckai |
| 8,382,753 B2 | 2/2013 | Truckai |
| 8,500,732 B2 | 8/2013 | Truckai et al. |
| 8,540,708 B2 | 9/2013 | Truckai et al. |
| 8,690,873 B2 | 4/2014 | Truckai et al. |
| 8,821,486 B2 | 9/2014 | Toth et al. |
| 8,998,901 B2 | 4/2015 | Truckai et al. |
| 2002/0022870 A1 | 2/2002 | Truckai et al. |
| 2002/0058933 A1 | 5/2002 | Christopherson et al. |
| 2002/0068934 A1 | 6/2002 | Edwards et al. |
| 2002/0082635 A1 | 6/2002 | Kammerer et al. |
| 2003/0130655 A1 | 7/2003 | Woloszko et al. |
| 2003/0153905 A1 | 8/2003 | Edwards et al. |
| 2003/0171743 A1 | 9/2003 | Tasto et al. |
| 2003/0176816 A1 | 9/2003 | Maguire et al. |
| 2003/0208200 A1 | 11/2003 | Palanker et al. |
| 2003/0216725 A1 | 11/2003 | Woloszko et al. |
| 2004/0002702 A1 | 1/2004 | Xiao et al. |
| 2004/0010249 A1 | 1/2004 | Truckai et al. |
| 2004/0087936 A1 | 5/2004 | Stern et al. |
| 2004/0215180 A1 | 10/2004 | Starkebaum et al. |
| 2004/0215182 A1 | 10/2004 | Lee |
| 2004/0215296 A1 | 10/2004 | Ganz et al. |
| 2004/0230190 A1 | 11/2004 | Dahla et al. |
| 2005/0075630 A1 | 4/2005 | Truckai et al. |
| 2005/0165389 A1 | 7/2005 | Swain et al. |
| 2005/0182397 A1 | 8/2005 | Ryan |
| 2005/0192652 A1 | 9/2005 | Cioanta et al. |
| 2005/0228372 A1 | 10/2005 | Truckai et al. |
| 2005/0240176 A1 | 10/2005 | Oral et al. |
| 2005/0251131 A1 | 11/2005 | Lesh |
| 2006/0009756 A1 | 1/2006 | Francischelli et al. |
| 2006/0052771 A1 | 3/2006 | Sartor et al. |
| 2006/0084969 A1 | 4/2006 | Truckai et al. |
| 2006/0089637 A1 | 4/2006 | Werneth et al. |
| 2006/0189971 A1 | 8/2006 | Tasto et al. |
| 2006/0189976 A1 | 8/2006 | Karni et al. |
| 2006/0224154 A1 | 10/2006 | Shadduck et al. |
| 2006/0259025 A1 | 11/2006 | Dahla |
| 2007/0021743 A1 | 1/2007 | Rioux et al. |
| 2007/0083192 A1 | 4/2007 | Welch |
| 2007/0161981 A1 | 7/2007 | Sanders et al. |
| 2007/0213704 A1 | 9/2007 | Truckai et al. |
| 2007/0282323 A1 | 12/2007 | Woloszko et al. |
| 2007/0287996 A1 | 12/2007 | Rioux |
| 2007/0288075 A1 | 12/2007 | Dowlatshahi |
| 2007/0293853 A1 | 12/2007 | Truckai et al. |
| 2008/0058797 A1 | 3/2008 | Rioux |
| 2008/0091061 A1* | 4/2008 | Kumar ............... A61B 1/00068 600/104 |
| 2008/0097242 A1 | 4/2008 | Cai |
| 2008/0097425 A1 | 4/2008 | Truckai |
| 2008/0125765 A1 | 5/2008 | Berenshteyn et al. |
| 2008/0125770 A1 | 5/2008 | Kleyman |
| 2008/0154238 A1 | 6/2008 | McGuckin |
| 2008/0183132 A1 | 7/2008 | Davies et al. |
| 2008/0208189 A1 | 8/2008 | Van Wyk et al. |
| 2008/0221567 A1 | 9/2008 | Sixto et al. |
| 2008/0249518 A1 | 10/2008 | Warnking et al. |
| 2008/0281317 A1 | 11/2008 | Gobel |
| 2009/0048593 A1 | 2/2009 | Ganz et al. |
| 2009/0054888 A1 | 2/2009 | Cronin |
| 2009/0054892 A1 | 2/2009 | Rioux et al. |
| 2009/0076494 A1 | 3/2009 | Azure |
| 2009/0105703 A1 | 4/2009 | Shadduck |
| 2009/0131927 A1 | 5/2009 | Kastelein et al. |
| 2009/0149846 A1 | 6/2009 | Hoey et al. |
| 2009/0163908 A1 | 6/2009 | MacLean et al. |
| 2009/0209956 A1 | 8/2009 | Marion |
| 2009/0306654 A1 | 12/2009 | Garbagnati |
| 2010/0004595 A1 | 1/2010 | Nguyen et al. |
| 2010/0036372 A1 | 2/2010 | Truckai et al. |
| 2010/0042095 A1 | 2/2010 | Bigley et al. |
| 2010/0042097 A1 | 2/2010 | Newton et al. |
| 2010/0049190 A1 | 2/2010 | Long et al. |
| 2010/0100091 A1 | 4/2010 | Truckai |
| 2010/0100094 A1 | 4/2010 | Truckai |
| 2010/0106152 A1 | 4/2010 | Truckai et al. |
| 2010/0114089 A1 | 5/2010 | Truckai et al. |
| 2010/0121319 A1 | 5/2010 | Chu et al. |
| 2010/0125269 A1 | 5/2010 | Emmons et al. |
| 2010/0137855 A1 | 6/2010 | Berjano et al. |
| 2010/0137857 A1 | 6/2010 | Shroff et al. |
| 2010/0152725 A1 | 6/2010 | Pearson et al. |
| 2010/0185191 A1 | 7/2010 | Carr et al. |
| 2010/0198214 A1 | 8/2010 | Layton, Jr. |
| 2010/0204688 A1 | 8/2010 | Hoey et al. |
| 2010/0217256 A1 | 8/2010 | Strul et al. |
| 2010/0228239 A1 | 9/2010 | Freed |
| 2010/0228245 A1 | 9/2010 | Sampson et al. |
| 2010/0286680 A1 | 11/2010 | Kleyman |
| 2011/0004205 A1 | 1/2011 | Chu et al. |
| 2011/0060391 A1 | 3/2011 | Unetich et al. |
| 2011/0112524 A1 | 5/2011 | Stern et al. |
| 2011/0282340 A1 | 11/2011 | Toth et al. |
| 2012/0041434 A1 | 2/2012 | Truckai |
| 2012/0041437 A1 | 2/2012 | Truckai |
| 2012/0116384 A1 | 5/2012 | Truckai |
| 2012/0130361 A1 | 5/2012 | Toth et al. |
| 2012/0330292 A1 | 12/2012 | Shadduck et al. |
| 2013/0172870 A1 | 7/2013 | Germain et al. |
| 2013/0267937 A1 | 10/2013 | Shadduck et al. |
| 2013/0345705 A1 | 12/2013 | Truckai et al. |
| 2014/0012249 A1 | 1/2014 | Truckai et al. |
| 2014/0303611 A1 | 10/2014 | Shadduck et al. |
| 2014/0336632 A1 | 11/2014 | Toth et al. |
| 2014/0336643 A1* | 11/2014 | Orczy-Timko .... A61B 18/1447 606/45 |
| 2015/0105791 A1 | 4/2015 | Truckai |
| 2015/0119795 A1* | 4/2015 | Germain ............. A61M 3/0229 604/28 |
| 2015/0182281 A1 | 7/2015 | Truckai et al. |
| 2016/0095615 A1 | 4/2016 | Orczy-Timko et al. |

FOREIGN PATENT DOCUMENTS

| | | |
|---|---|---|
| EP | 1595507 A2 | 11/2005 |
| WO | WO-0053112 A2 | 9/2000 |
| WO | WO-2005122938 A1 | 12/2005 |
| WO | WO-2006001455 A1 | 1/2006 |
| WO | WO-2008083407 A1 | 7/2008 |

(56) References Cited

FOREIGN PATENT DOCUMENTS

WO    WO-2011053599 A1    5/2011
WO    WO-2014165715 A1    10/2014

OTHER PUBLICATIONS

European search report and search opinion dated Jul. 10, 2013 for EP Application No. 10827399.
International search report and written opinion dated Feb. 2, 2011 for PCT/US2010/056591.
International search report and written opinion dated Dec. 10, 2009 for PCT/US2009/060703.
International search report and written opinion dated Dec. 14, 2010 for PCT/US2010/054150.
International Search Report dated Sep. 10, 2014 for PCT/US2014/032895.
Notice of allowance dated Jan. 9, 2014 for U.S. Appl. No. 13/938,032.
Notice of allowance dated Feb. 25, 2015 for U.S. Appl. No. 13/975,139.
Notice of allowance dated Mar. 5, 2012 for U.S Appl. No. 13/281,846.
Notice of allowance dated Mar. 5, 2012 for U.S. Appl. No. 13/281,856.
Notice of allowance dated Mar. 29, 2013 for U.S. Appl. No. 12/605,546.
Notice of allowance dated May 9, 2014 for U.S. Appl. No. 12/944,466.
Notice of allowance dated May 24, 2013 for U.S. Appl. No. 12/605,929.
Notice of allowance dated Nov. 15, 2012 for U.S. Appl. No. 12/541,043.
Notice of allowance dated Nov. 15, 2012 for U.S. Appl. No. 12/541,050.
Notice of allowance dated Dec. 2, 2014 for U.S. Appl. No. 13/975,139.
Office action dated Jan. 28, 2013 for U.S. Appl. No. 12/605,546.
Office action dated Feb. 4, 2016 for U.S. Appl. No. 13/857,068.
Office action dated Mar. 12, 2012 for U.S. Appl. No. 12/541,043.
Office action dated Mar. 12, 2012 for U.S. Appl. No. 12/541,050.
Office action dated Mar. 31, 2016 for U.S. Appl. No. 13/281,805.
Office action dated Apr. 24, 2014 for U.S. Appl. No. 13/975,139.
Office action dated May 22, 2015 for U.S. Appl. No. 14/657,684.
Office action dated Jun. 5, 2015 for U.S. Appl. No. 13/857,068.
Office action dated Jun. 18, 2012 for U.S. Appl. No. 12/605,546.
Office action dated Jul. 23, 2015 for U.S. Appl. No. 13/281,805.
Office action dated Sep. 22, 2014 for U.S. Appl. No. 13/281,805.
Office action dated Sep. 24, 2015 for U.S. Appl. No. 13/236,471.
Office action dated Sep. 28, 2012 for U.S. Appl. No. 12/541,043.
Office action dated Sep. 28, 2012 for U.S. Appl. No. 12/541,050.
Office action dated Sep. 28, 2012 for U.S. Appl. No. 12/605,929.
Office action dated Oct. 9, 2014 for U.S. Appl. No. 13/857,068.
Office action dated Oct. 24, 2014 for U.S. Appl. No. 13/975,139.
Office action dated Nov. 6, 2013 for U.S. Appl. No. 13/938,032.
Office action dated Dec. 4, 2014 for U.S. Appl. No. 13/236,471.
Office action dated Dec. 6, 2011 for U.S. Appl. No. 13/281,846.
Office action dated Dec. 16, 2014 for U.S. Appl. No. 13/281,805.
Office action dated Dec. 22, 2011 for U.S. Appl. No. 13/281,856.
Office action dated Apr. 22, 2016 for U.S. Appl. No. 14/657,684.

\* cited by examiner

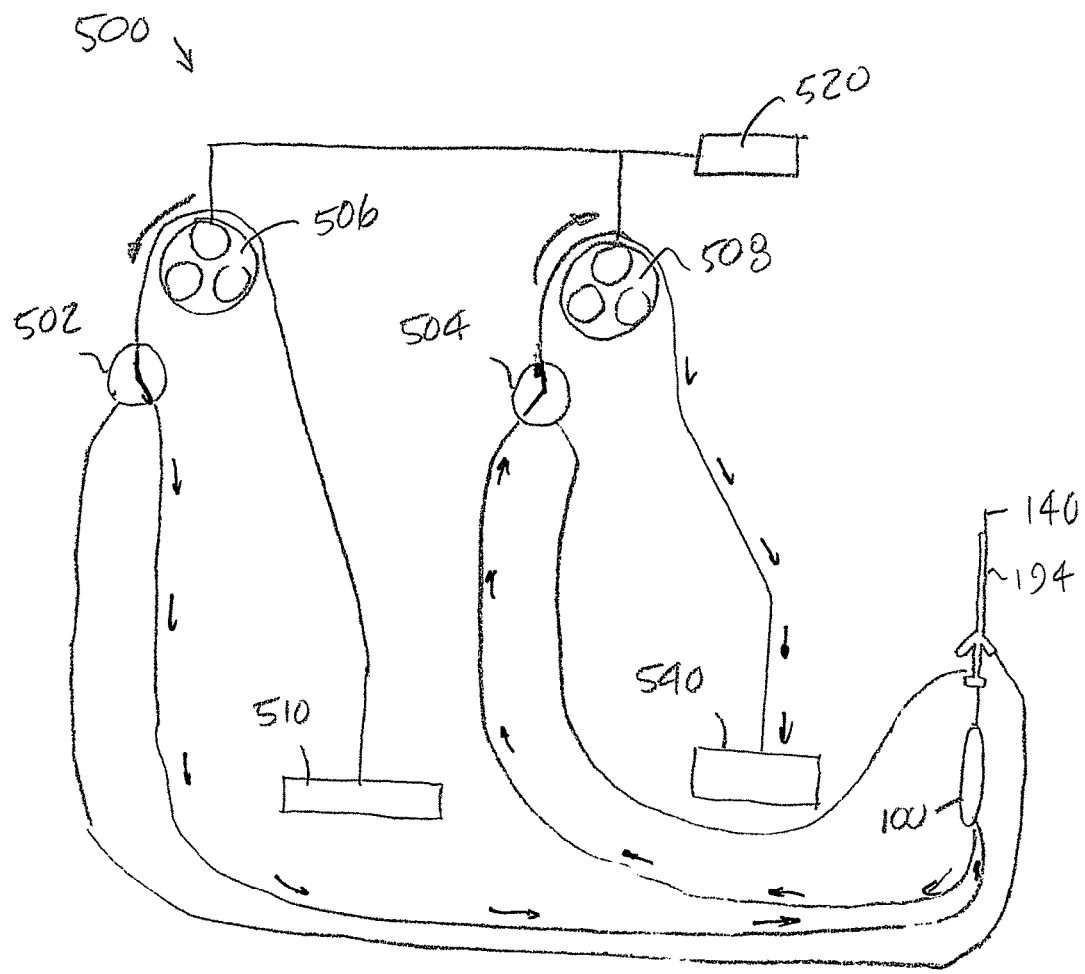
FIG_13B

SURGICAL FLUID MANAGEMENT SYSTEM AND METHOD OF USE

CROSS-REFERENCE TO RELATED APPLICATIONS

This application claims the benefit of and priority to Provisional Application No. 62/107,953, filed Jan. 26, 2015, the entire content of which is incorporated herein by reference.

BACKGROUND OF THE INVENTION

The present invention relates to fluid management systems and devices for resecting and removing tissue from the interior of a patient's body, for example in a transurethral resection of prostate tissue to treat benign prostatic hyperplasia.

Many electrosurgical and other minimally invasive procedures are performed though endoscopes which introduce an electrosurgical tool to target tissue via a body lumen or cavity. For example, prostate tissue resection may be performed using an electrosurgical resection tool which is placed using an endoscope located via the urethra. In such instances, it is often necessary to introduce saline or another fluid both to the body lumen in to create a working space and provide visibility and to the working end of the resection tool to enhance resection and/or collect debris.

Heretofore, fluids have often been introduced using a saline drip to the body lumen and/or the tissue resection area. The use of saline drips is simple but often lacks a degree of control and accountability that would be desirable. Active pumping systems have also been proposed, but such systems are frequently complicated and bulky, and often two separate pumping systems are needed to deliver separate fluid flows to the body lumen/cavity and to the tissue resection area.

For these reasons, it would be desirable to provide improved and alternative fluid management systems and methods which can be compact, easy to operate, and which minimize the need for redundant hardware. It would further desirable if such systems and methods allowed a simplified ability to keep track of fluid accumulation in the patient. At least some of these objectives will be met by the inventions described and claimed below.

SUMMARY OF THE INVENTION

In a first aspect of the present invention, a fluid management system is configured to receive fluid from a fluid source, to deliver fluid to a medical probe having a first fluid infusion and aspiration circuit and a second fluid infusion and aspiration circuit, and to transfer fluid from the medical probe to a collection container. The fluid management system comprises a first pump and valve assembly, a second pump and valve assembly, and a controller. The controller is configured to operate the first pump and valve assembly to selectively provide fluid inflow from the fluid source to one of the first fluid infusion and aspiration circuit of the medical probe and the second fluid infusion and aspiration circuit of the medical probe. The controller is further configured to operate the second pump and valve assembly to selectively transfer fluid outflow to the collection container from one of the first fluid infusion and aspiration circuit of the medical probe and the second fluid infusion and aspiration circuit of the medical probe.

In a first specific embodiment of the fluid management system, the pump of the first pump and valve assembly is operable to reverse flow direction and the valves of the first pump and valve assembly include a pair of one-way valves oriented to provide inflow to the pump from the fluid source in both flow directions. A pump of the second pump and valve assembly may also be operable to reverse flow direction where the valves of the second pump and valve assembly include a pair of one-way valves oriented to provide outflow from the pump to the first fluid infusion and aspiration circuit of the medical probe when the pump is operated in a first flow direction and to provide outflow from the pump to the second fluid infusion and aspiration circuit of the medical probe when the pump is operated in a second flow direction. The one-way valves are adapted to direct fluid flows between first and second flow paths in response to the first and second flow directions established by the pumps.

In an alternative specific embodiment of the fluid management system, the pumps of the first and second pump and valve assemblies are each operable to deliver flow in a single flow direction and the valves of the first and second pump and valve assemblies include three-way valves that are selectively positionable by the controller to (1) deliver fluid inflow from the fluid source to one of the first fluid infusion and aspiration circuit of the medical probe or the second fluid infusion and aspiration circuit of the medical probe and to (2) provide fluid outflow to the collection container from one of the first fluid infusion and aspiration circuit of the medical probe and the second fluid infusion and aspiration circuit of the medical probe.

In still other embodiments of the fluid management system of the present invention, the controller may be further configured to maintain a fluid operating parameter delivered by the fluid management system within a pre-determined range. The fluid operating parameter may consists of a first pump speed, a second pump speed, and a targeted pressure delivered to the first fluid infusion and aspiration circuit of the medical probe. The fluid operating parameter may be established by a first pump speed, a second pump speed, and a targeted pressure delivered to the second fluid infusion and aspiration circuit of the medical probe.

In yet further embodiments of the fluid management system of the present invention, the first and second pumps are peristaltic pumps, and the peristaltic pumps may be operable in a first rotational direction to deliver fluid inflow and collect fluid outflow from the first fluid infusion and aspiration circuit of the medical probe. The pumps will usually also be operable in a second rotational direction to deliver fluid inflow and collect fluid outflow from the second fluid infusion and aspiration circuit of the medical probe. The first and second pump and valve assemblies may include tubing sets that carry the valves, and the valves may be one-way valves.

The fluid management systems of the present invention may be incorporated into minimally invasive surgical systems which further comprise a viewing scope having a working channel and including the first fluid infusion and aspiration circuit. Such minimally invasive surgical systems may also comprise a surgical tool configured to be introduced through the working channel of the viewing scope and including the second fluid infusion and aspiration circuit.

In a second aspect of the present invention, an electrosurgical resection method for treating a patient's prostate comprises (1) providing a fluid management wherein a pump system circulates fluid in a first path through a transurethral device to allow endoscopic viewing within the prostate urethra and (2) providing a fluid management wherein a pump system circulates fluid in a second path to through a transurethral device to assist in electrosurgical tissue resection. The first and second providing steps may provided by first and second independent fluid management systems or, alternatively, may be provided by a single fluid management system configured to operate in first and second modes.

In a third aspect of the present invention, an electrosurgical method for resecting a patient's tissue comprises establishing an inflow of fluid using a first pump and establishing an outflow of fluid using a second pump. The inflow of fluid from the first pump is directed both to a viewing scope in a patient lumen or body cavity and to a resection tool engaged with target tissue. The outflow of fluid from the viewing scope in the patient lumen or body cavity as well as from the resection tool engaged with the target tissue is collected using the second pump. In specific embodiments of the electrosurgical methods, the inflow of fluid is selectively directed to the viewing scope by operating the first pump in a first flow direction and to the resection tool by operating the first pump in a second flow direction. The outflow of fluid may be selectively collected from the viewing scope by operating the second pump in a first flow direction and from the resection tool by operating the second pump in a second flow direction. Typically, the first pump comprises a rotary peristaltic pump configured to be selectively driven in first and second rotational directions, and the second pump comprises a rotary peristaltic pump configured to be selectively driven in first and second rotational directions.

BRIEF DESCRIPTION OF DRAWINGS

FIG. 13B is a diagram of the fluid management system of FIG. 13A that is operating in a second mode to provide fluid flows to a second working space.

DETAILED DESCRIPTION OF THE INVENTION

Figure 1:
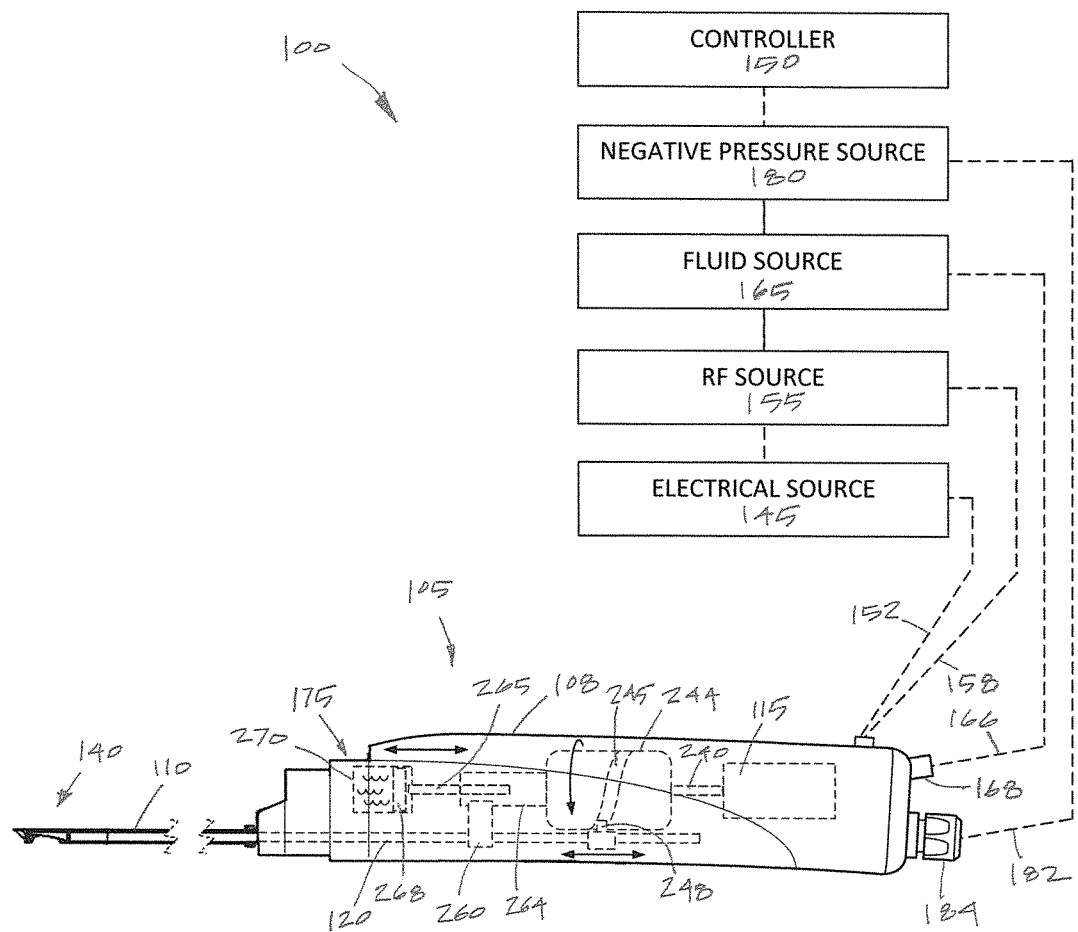
FIG. 1 is a side view of a tissue resecting probe and block diagram of systems and operating components corresponding to the invention.
Figure 2:
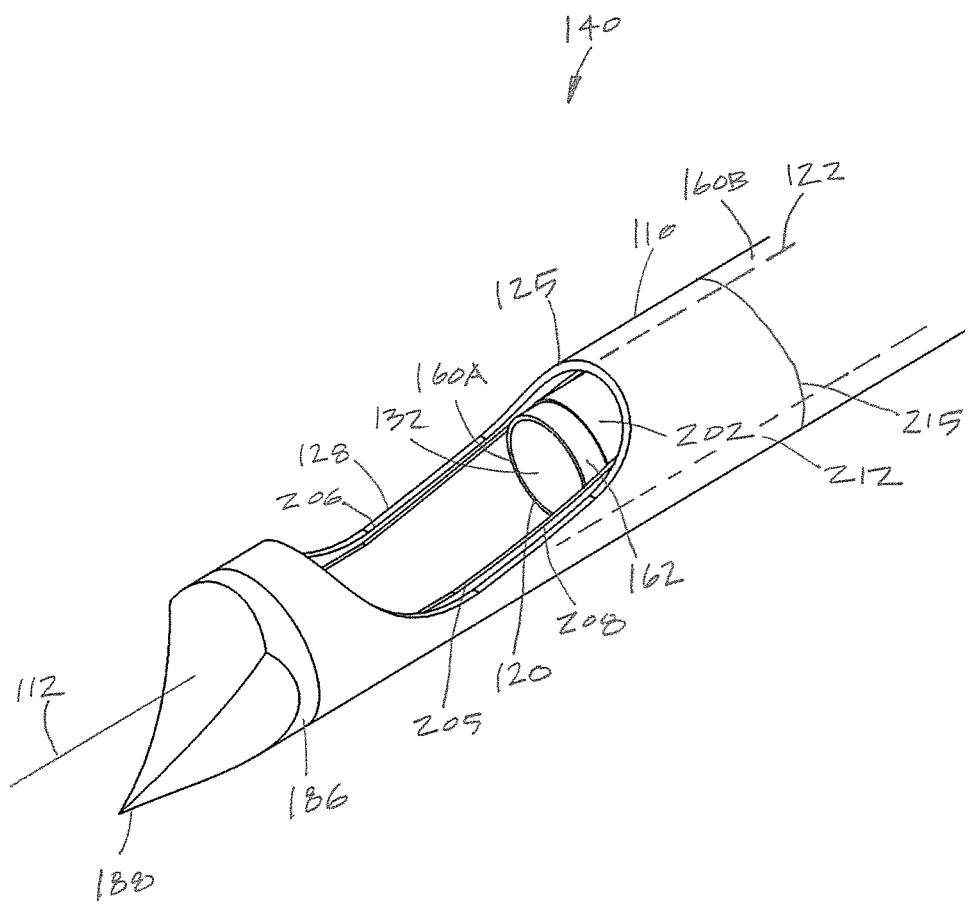
FIG. 2 is a perspective view of the working end of the resecting probe of FIG. 1 showing the inner resecting sleeve in a proximal or retracted position providing a window-open position.
Figure 3:
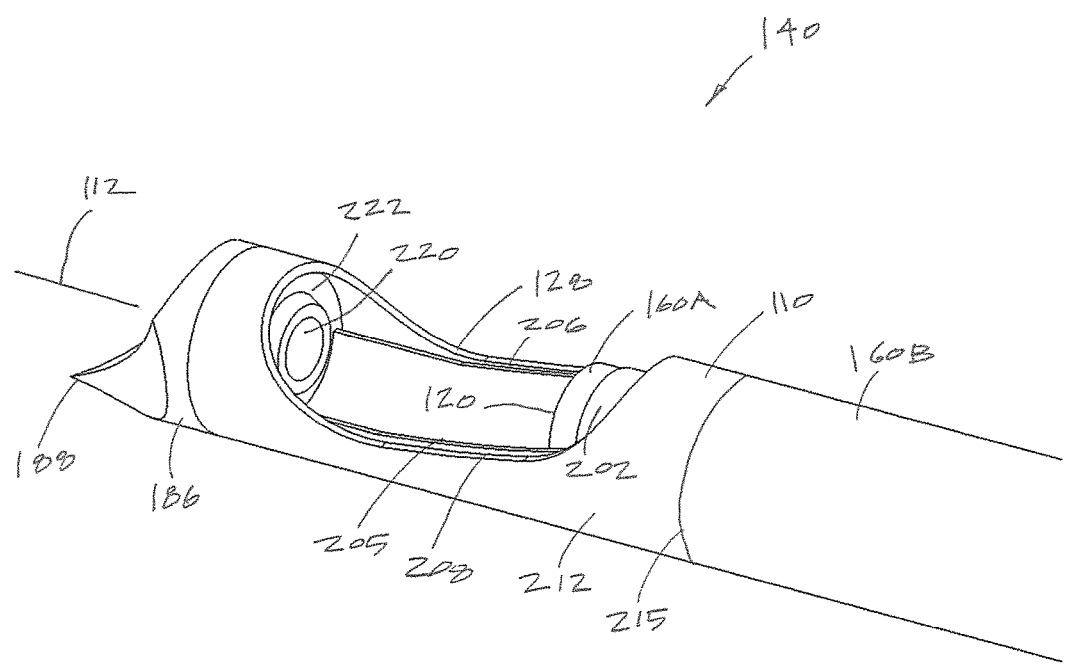
FIG. 3 is another perspective view of the working end of the resecting probe of FIG. 1 showing a resilient element that interfaces with the reciprocating inner sleeve at the distal end of its stroke.

FIGS. 1-3 illustrate an electrosurgical tissue resecting system 100 that includes a hand-held single-use tissue resecting device or probe 105. The device 105 has a handle portion 108 that is coupled to an elongated shaft or extension portion 110 that has an outer diameter ranging from about 2 mm to 5 mm. In one variation, the device is adapted for performing a TURP procedure (transurethral resection of the prostate) and the shaft portion 110 extending about longitudinal axis 112 can have a length suitable for introducing though an endoscope or cystoscope to thereby access a male patient's prostate to resect and remove tissue.

Referring to FIG. 1, it can be seen that the handle 108 carries an electric motor 115 for reciprocating or rotating a resecting element, which in the variation of FIG. 1-3 is an inner sleeve 120 that reciprocates in a passageway 122 defined within the interior of an outer sleeve 125 to resect tissue interfacing window 128 in the outer sleeve. Resected tissue slugs are captured in channel 132 in inner sleeve 120 and can be extracted or moved in the proximal direction in the channel by both positive and negative pressures on either side of the tissue slug as will be described below. FIGS. 2-3 illustrate the working end 140 of the resecting device 105 with the moveable inner resecting sleeve 120 in a retracted position relative to window 128. The motor 115 in handle 108 is operatively coupled to an electrical source 145 and controller 150 by electrical cable 152. The controller 125 can include algorithms adapted to control motor voltage which in turn can control the speed of reciprocation or rotation of the resecting sleeve 120 as will be described below.

Still referring to FIG. 1, the system 100 includes an RF source 155 operatively coupled by cable 158 to first and second opposing polarity electrodes 160A and 160B in the working end 140 (FIG. 2). The distal end 162 of inner sleeve 120 comprises a first or active electrode 160A which is adapted to form an electrosurgical plasma for resecting tissue as is known in the art. The second or return electrode 160B can comprise a medial portion of outer sleeve 125 and/or the distal tip component of the shaft portion 110.

Figure 4A:
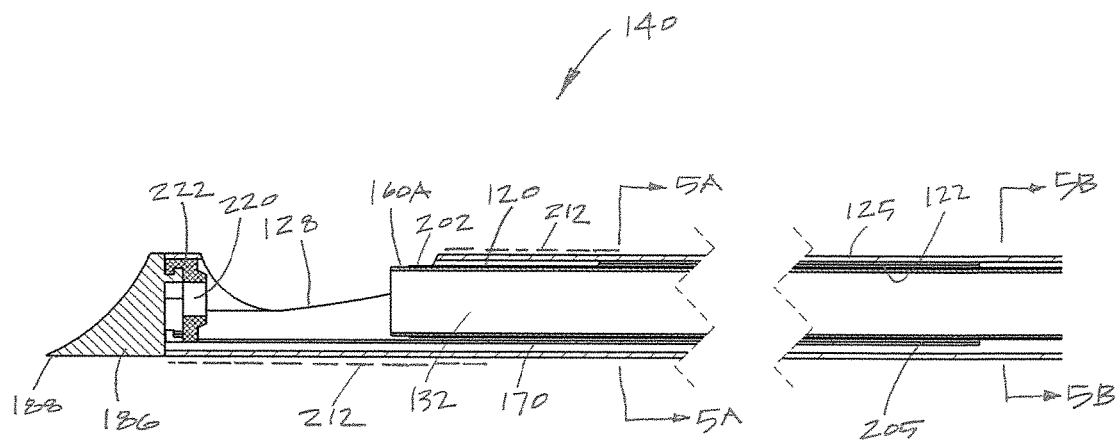
FIG. 4A is a sectional view of the working end of FIG. 2 with the reciprocating resecting sleeve in a proximal position at the beginning of its stroke in a window-open position.

FIG. 1 further illustrates that the system 100 includes a remote fluid source 165 which has flow line 166 extending to a coupling 168 in handle 108. The fluid source 165 can comprise a bag of saline and flow line 166 is in fluid communication with a flow channel 170 in the shaft portion 110 to carry fluid through to handle 108 to the working end 140 by means of a pump mechanism 175 carried in the handle 108 (FIG. 4A).

FIG. 1 also shows that the system 100 has a remote negative pressure source 180 that has suction line 182 that couples to fitting 184 in the handle 108. The negative pressure source 180 communicates with a tissue-extraction channel 132 in the resecting sleeve 120 for assisting in extracting tissue from the site of the resection, for example in the patient's prostate (see FIGS. 9-10)

As can be understood from FIG. 1, the controller 150 includes algorithms for operating and modulating the operating parameters of the subsystems, including the RF source 155, the fluid source 165 and associated pump mechanism 175, the negative pressure source 180 and the motor 115 via motor voltage. As will be described below, in some operating modes, the controller 150 may adjust operating parameters of all subsystems during each reciprocation cycle of the resecting sleeve 120 to achieve various operating objectives.

Now turning to FIGS. 4A-7B, the structure and operation of the working end 140 can be described. A similar device can be made with a sharp tip or a rounded tip for different approaches for prostate resection. In one variation shown in FIGS. 2-4B, it can be seen that the distal end body 186 with a sharp tip 188 of the device is sharp for penetrating tissue. In a resection procedure in a prostate 190 (see FIG. 10) such a sharp tip 188 is adapted for extending outward from the working channel 192 of an endoscope or cystoscope 194 to penetrate through the urethra 195 into a prostate lobe 196 under suitable imaging such as ultrasound. This method would spare the urethra 195 except for one or more puncture sites. In another embodiment shown in FIG. 9, the device can have a rounded distal tip 198 and the resection procedure can be started within the urethra 195 and progress outwardly into the prostate lobe 196 in a method similar to conventional TURP procedures which use an RF loop and which do not spare the urethra 195.

FIGS. 2, 3 and 4A-4B illustrate the movement of the resecting sleeve 120 and explain how the working end 140 is configured to resect tissue, for example in a prostate. Referring to FIGS. 2, 3 and 4A, the inner resecting sleeve 120 is typically fabricated of thin-wall stainless steel but any other suitable materials can be used. The inner sleeve 120 has a thin insulating coating 202 around it exterior except for a distal end portion 162 that comprises electrode 160A. The exposed distal portion 162 that comprises electrode 160A can have a length ranging from about 1 mm to 6 mm. In one variation, the inner sleeve has an OD of 0.106" and an ID of 0.098". The insulating coating is parylene, but other dielectric polymers or ceramic coating are possible, such as PFA, polytetrafluroethylene (PTFE), FEP (Fluorinated ethylenepropylene), polyethylene, polyamide, ECTFE (ethylenechlorotrifluoro-ethylene), ETFE, PVDF, polyvinyl chloride or silicone. The proximal end of inner resecting sleeve 120 is coupled to the electrical cable 158 within handle 108 and to a first pole of the RF source 155 (FIG. 1).

Figure 4B:
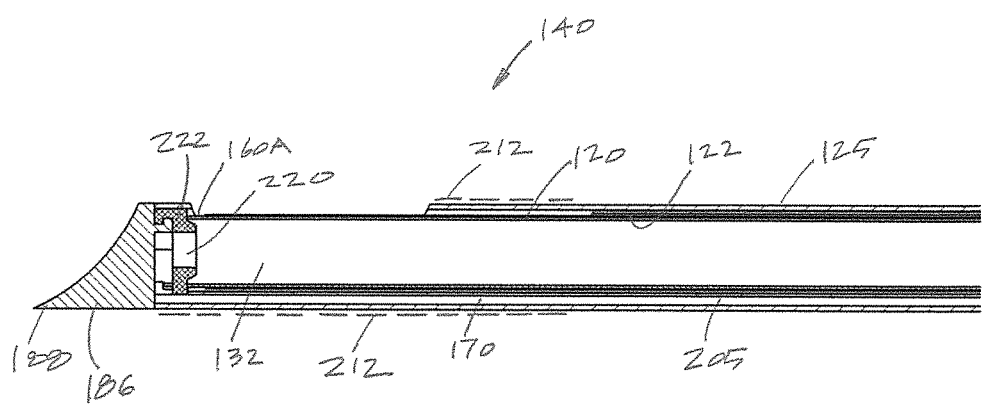
FIG. 4B is a sectional view of the working end as in FIG. 4A with the reciprocating resecting sleeve in a distal position at the end of its stroke in a window-closed position.
Figure 5A:
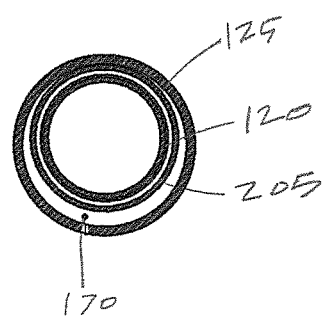
FIG. 5A is a sectional view of the shaft of the probe of FIG. 1 taken along line 5A-5A of FIG. 4A.
Figure 5B:
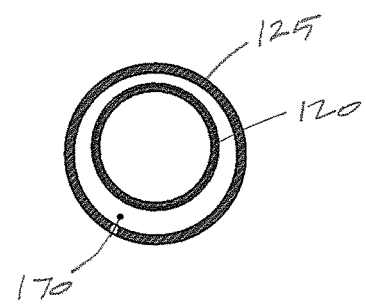
FIG. 5B is a sectional view of the shaft of the probe of FIG. 1 taken along line 5B-5B of FIG. 4A.

In FIGS. 2, 4A-4B and 5A-5B, it can be seen the outer sleeve 125 at the working end 140 comprises an assembly of outer sleeve 125 and thin wall intermediate sleeve 205 that when combined with outer sleeve 125 defines a flow channel 170 between the sleeves (see FIG. 5A). The intermediate sleeve 205 can extend to the handle 108 or can terminate in a medial region of shaft portion 110 as indicated in FIGS. 4A and 5B. Thus, it can be understood that inner sleeve 120 reciprocates in passageway 122 that is defined by intermediate sleeve 125. In FIGS. 2 and 3, it can be seen that the window 128 is defined by edges 206 and 208 of the outer sleeve 125 and intermediate sleeve 205, respectively, and the edges are welded or sealed by an insulating coating so that flow channel 170 has no open terminal portion around window 128. In FIGS. 4A-4B, a continuous parylene coating 212 (or other insulating coating) is provided about the exterior of outer sleeve and around the window 128 and in the passageway 122 in the intermediate sleeve 205. This coating 212 can extend proximally from the window from 5 mm to 50 mm to a terminal edge 215 (see FIGS. 2, 3 and 4A). Proximal to the edge 215 of the coating 212 on the outer sleeve is the exposed surface of outer sleeve 125 which comprises the return electrode 160B. The proximal end of inner resecting sleeve 120 is coupled to electrical cable 158 within handle 108 and thus to a second pole of the RF source 155.

Figure 8:
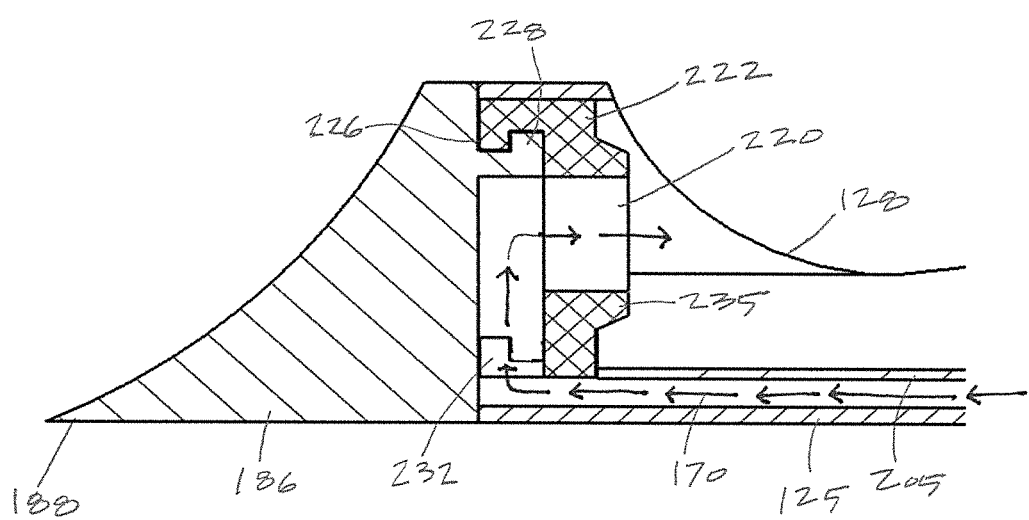
FIG. 8 is an enlarged sectional view of the distal portion of the window of the working end of FIGS. 2-3.

FIGS. 3, 4A-4B, and 8 illustrate that the flow channel 170 has a open termination 220 facing in the proximal direction in the center of dielectric element 222 that is fixed to distal end component 186. In one variation as shown in FIG. 8, the dielectric element 222 is of a resilient material such as silicone and with a circular edge 226 that fits over and grips metal edge 228 of the distal end component 186. In the enlarged view of FIG. 8, it can be seen that flow channel 170 transitions to gap 232 in the dielectric element 222 which allows fluid to flow from channel 170 through gap 232 and then in a reversed (proximal) direction through open termination 220. FIGS. 4A-4B and 8 show that dielectric element 222 has a circular ledge 235 around open termination 220 that is adapted to project slightly into and engage the electrode 160A and distal end 162 of inner sleeve 120 when this sleeve is at its distal-most position in each cycle of its reciprocation. The dielectric element 222 thus can form a seal with distal end 162 of the inner sleeve 120 at the distal-most position of its stroke. As will be described below, during a brief interval when inner sleeve 120 is at the end of its stroke and sealed against the dielectric element, then the pump mechanism 175 can provide a fluid flow burst through channel 170 and open termination 220 which causes resected tissue to be pushed proximally in tissue extraction channel 132 in inner sleeve 120.

Figure 6A:
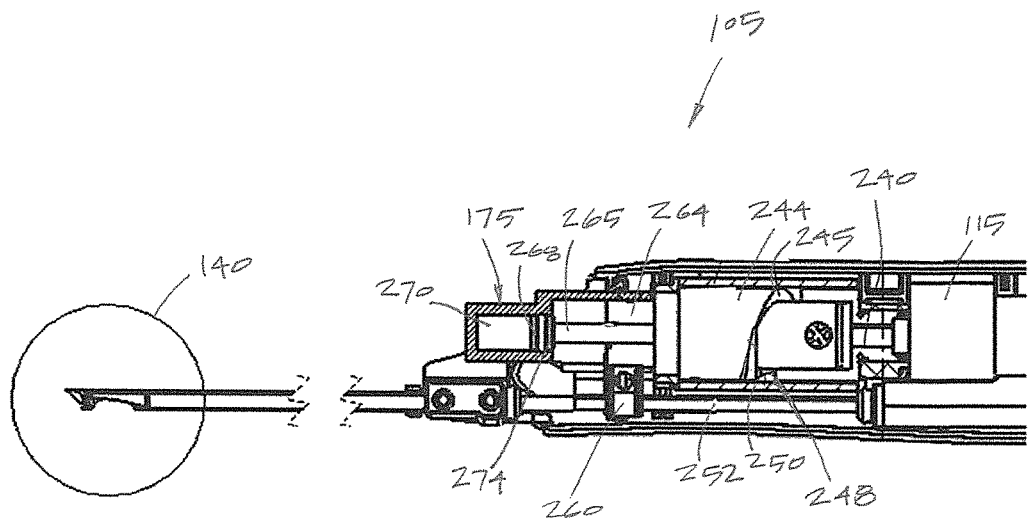
FIG. 6A is a longitudinal sectional view of the shaft and handle of the probe of FIG. 1 showing the motor and drive mechanism with the resecting sleeve at the beginning of its stroke in a window-open position.
Figure 6B:
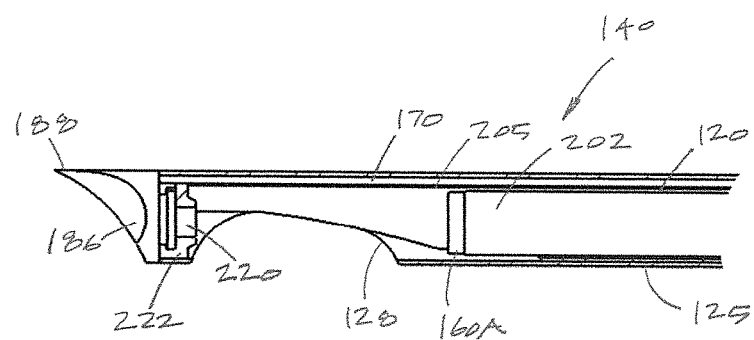
FIG. 6B is an enlarged sectional view of the working end of FIG. 6A with the resecting sleeve at the beginning of its stroke.
Figure 7A:
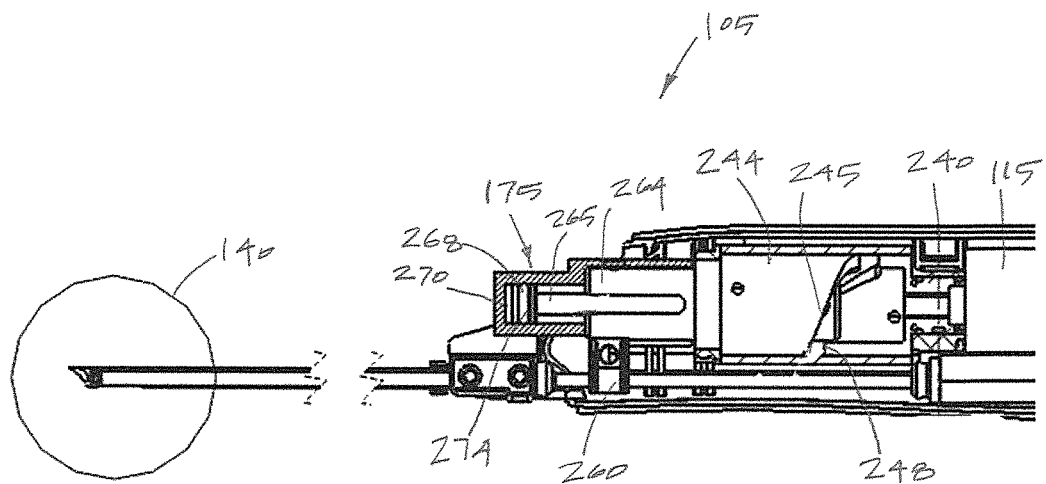
FIG. 7A is a longitudinal sectional view of the shaft and handle as in FIG. 6A showing the motor and drive mechanism with the resecting sleeve at the end of its stroke in a window-closed position.
Figure 7B:
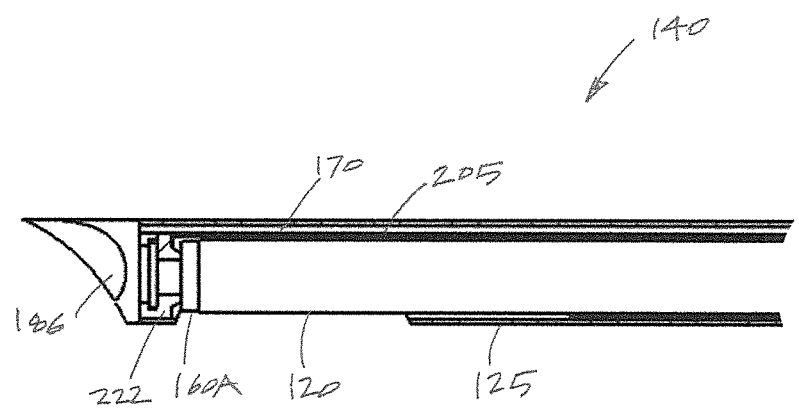
FIG. 7B is an enlarged sectional view of the working end of FIG. 7A with the resecting sleeve at the end of its stroke.

FIGS. 1, 6A and 7A show in general indicate how the single motor 115 in handle operates to both reciprocate the inner resecting sleeve 120 and the pump mechanism 175. In FIG. 6A, it can seen that motor 115 together with an internal gear reduction mechanism rotates shaft 240 which is coupled to a rotating drive collar 244 which converts rotary motion to axial motion. An arcuate or partly helical slot 245 in the drive collar 244 cooperates with a pin 248 in non-rotating body 250 that is keyed in the handle 108 and fixed to the proximal end 252 of the inner resecting sleeve 120. The motor 115 can comprise any suitable electrical motor, for example, a brushless electric motor. The motor 115 (and operation of other subsystems) can be actuated by a user-operated switch, which typically is a footswitch but also could be a handswitch. As can be understood from FIGS. 6A-7B, the rotation of drive collar 244 will cause non-rotating body 250 to reciprocate and cause the inner sleeve 120 to move between the window-open position of FIGS. 6A-6B and the window-closed position of FIGS. 7A-7B. In one variation, referring to FIGS. 6A-7B, the drive collar 244 can rotate 360° with a continuous arcuate slot 245 to thus move the inner resecting sleeve 120 in a mechanical manner both in the distal direction to resect tissue captured in the window and in the proximal direction to re-open the window. In another embodiment, the drive collar 244 can operate as a cam to move the inner sleeve in the distal direction while also loading a spring mechanism (not shown), and then the spring mechanism can move the inner sleeve in the proximal direction back to the window-open position.

The speed of motor 115 can be constant through a cycle of reciprocation at a rate between 1 Hz to 5 Hz, or the controller 150 can use an algorithm to alter motor voltage to cause the motor to move the inner sleeve forward (distal direction) to resect tissue at a first speed and then move backward (proximal direction) at a second speed. In one variation as further described below, the controller 150 can control the RF source 155 to provide a constant power level which is adapted to generate a plasma about electrode 160A for resecting tissue during the forward stroke and then the same plasma can be used on the backward stroke to coagulate the tissue surface. In this variation, the backward stroke can be slowed down to provide a longer interval in which electrode 160A contacts tissue to increase the depth of coagulation. In the variation just described, motor voltage was modulated to alter the speed of the inner sleeve. It should be appreciated that the drive sleeve can rotate at a constant rate and the arcuate slot 245 in drive collar 244 and the cooperating pin 248 can be designed to provide the inner sleeve 120 with different effective forward and backward speeds. This would achieve the same result as modulating motor voltage to alter reciprocating speed.

FIGS. 1, 6A and 6B also illustrate how the motor 115 in handle 108 actuates the pump mechanism 175. In FIG. 6A, it again can seen that motor 115 rotates the drive collar 244 which in turn engaged pin 248 and causes the non-rotating body 250 to reciprocate. FIG. 6A also shows an actuator 260 fixed to the inner sleeve 120 within handle 108 that reciprocates to drive the pump mechanism 175. Referring to FIGS. 6A and 7A, the actuator 260 extends laterally and is coupled to cylindrical element 264 that also reciprocates in the handle 108, with part of its stroke extending into a bore in the drive collar 244. The cylindrical element 264 is coupled to shaft 265 of a piston 268 that moves back and forth in pump chamber 270 to thereby pump fluid from fluid source 165 through channel 170 (FIGS. 4A-5B) to the working end 140. It can be seen that piston 268 has o-rings 274 to seal the pump chamber 270 and fluid can be delivered to the pump mechanism through flow line 166 (FIG. 1) by gravity or other suitable means such as a pump. The fluid flows into and out of the pump chamber 270 can be facilitated by one-way valves are known in the art.

In the variation shown in FIGS. 6A-7B, the pump system 175 is actuated by the drive collar 244 which operates the resecting sleeve 120, and thus the reciprocation rate and/or the varied speed of the piston shaft 256 will match that of the resecting sleeve. The flow rate of fluid through the system will then be determined by the selected speed profile of the inner sleeve's reciprocation. In another variation, it is preferable to have a pulse of fluid flow through channel 170 and open termination 220 within a very brief time interval when then inner sleeve 120 is at the end of its stroke and sealed against the dielectric element 222. In this variation, the pulse of liquid can range from 1 cc to about 5 cc and is adapted to push a slug of resected tissue under positive pressure in the proximal direction in the tissue extraction channel 132. In order to provide such a pulsed flow, the drive collar 244 can have a second arcuate slot to drive a second pin (not shown) to drive the piston shaft 265 with any selected interval. In one variation, the pulse of fluid flow occurs within less than 0.2 seconds or less than 0.1 seconds. In another embodiment, the drive collar 244 can operate both the resecting sleeve 120 and the piston shaft 265 in unison and the fluid can flow into an intermediate reservoir in handle 108 (not shown) which can be configured to release the fluid into channel 170 only within a selected time interval.

Figure 9:
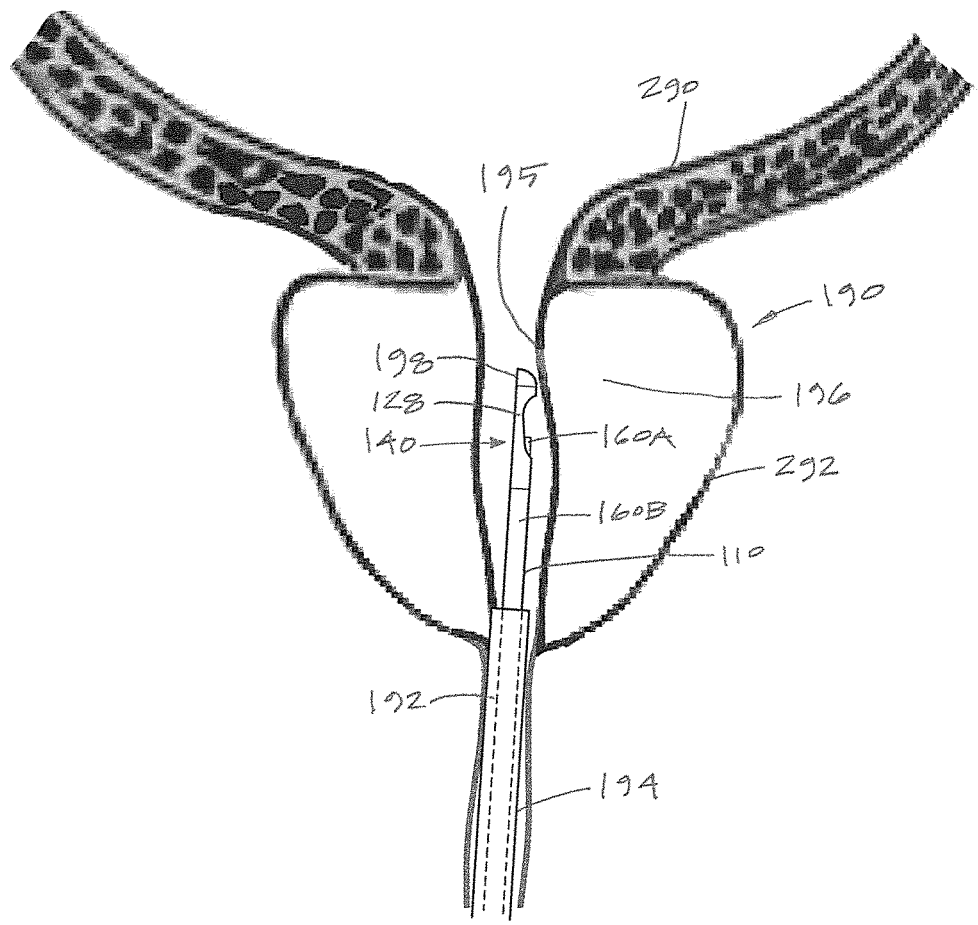
FIG. 9 is an illustration of a method of using a device similar to that of FIG. 1 in a tissue resection procedure in a patient's prostate, wherein the resection is initiated within the urethra.

FIG. 9 illustrates a step in a method of using the device 100 of FIG. 1 to resect tissue in a patient's prostate. In the method of FIG. 9, the physician introduces a cystoscope 194 transurethrally to view the prostate. The shaft 110 of a rounded end probe 100 is advanced through the working channel 192 of the cystoscope and after viewing appropriate landmarks as known in the art, the device is actuated to resect and extract tissue. In this method, a saline irrigation fluid is controllably delivered by a pump (or gravity flow) to the site through another channel in the cystoscope to immerse the treatment site in saline. In operation, the negative pressure source 180 can be actuated continuously, which communicates with tissue extraction channel 132 in the inner sleeve and functions to draw tissue into window 128. At the same time, the negative pressure source 180 will remove saline from site when the window is open to thus cause circulation of fluid through the treatment site, which will remove blood and debris to keep the saline clean for enhancing endoscopic viewing of the resection procedure. The saline inflows can be managed by any conventional fluid management system as is known in the art, wherein such systems include pressure sensing or pressure calculation mechanisms for monitoring and controlling fluid pressure in the treatment site. The working end 140 then can be moved axially and rotationally under direct endoscopic vision while the resecting sleeve 120 is actuated to resect and extract tissue. As described above, the actuation of a switch, such as a foot pedal will cause the controller to actuate (i) reciprocation of the resection sleeve 120, (ii) the pump mechanism 175, (iii) the negative pressure source 180, and the RF source 155. In one variation, the RF source 155 is controlled to operate continuously at a power level that created a plasma about electrode 160A to resect tissue as the sleeve 120 moves in the distal direction across window 128. In this variation, the plasma about electrode 160A coagulates tissue in contact with the electrode 160A as it moves in the proximal direction. The resected tissue slugs are captured in a collection container (not shown). In other methods of coagulating tissue in TURP procedure shown in FIG. 9, (i) the resecting sleeve can be moved in the proximal direction at a slower speed to allow the plasma about electrode 160 to be in contact with tissue for a longer interval, (ii) the controller can switch the output and/or power from RF source 155 to a different parameter for better coagulation on the return stroke of the resecting sleeve 120, and/or (iii) the resecting sleeve 120 can be stopped in a selected position within window 128 and the RF output and power can be delivered between electrodes 160A and 160B to allow the physician to manipulate the working end to coagulate targeted tissue. In the event that the system is operated in different modes, for example a plasma resection mode and a coagulation mode, then a conventional electrosurgical foot pedal system may be used with a first pedal for tissue resection and a second pedal for coagulation.

Figure 10:
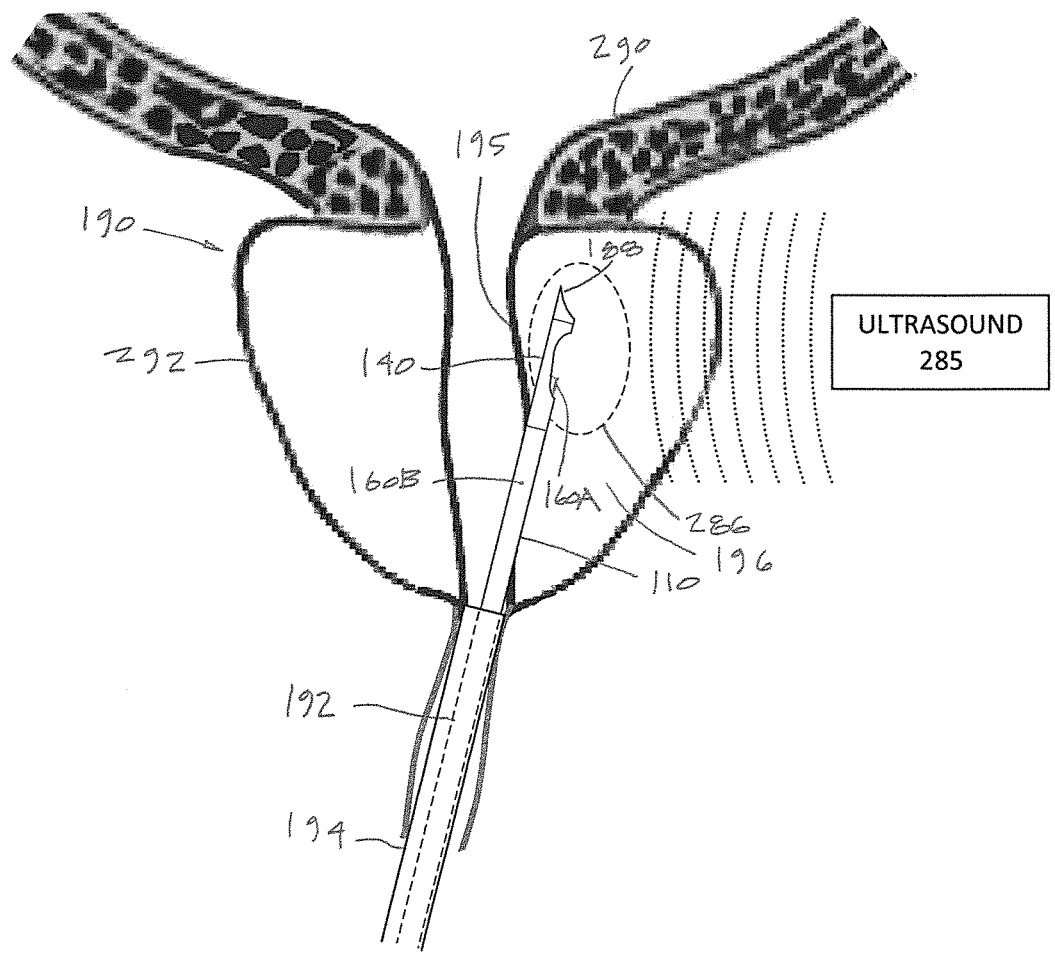
FIG. 10 is an illustration of an alternative method of using the device of FIG. 1 in a tissue resection procedure in a patient's prostate wherein the distal end is penetrated into the lobe of the prostate.

FIG. 10 illustrates another method of using device 100 of FIG. 1 to resect tissue in a patient's prostate. In the method of FIG. 10, the physician again introduces a cystoscope 194 transurethrally into a patient's prostate, and then advances shaft 110 of a sharp-tipped probe 100 through the working channel 192 of the cystoscope and thereafter through the urethra 195 into the prostate lobe 196. In this method, FIG. 10 shows that the tissue resection is done interstitially and thus viewing is needed which can be provided by ultrasound system 285 or another suitable type of imaging. In one variation, the ultrasound system is a TRUS system as known in the art. A conventional fluid management system can be used as described above to irrigate and maintain fluid pressure in the urethra 195. In FIG. 10, a target of the treatment is to resect and extract tissue region 286 wherein fluid from within the urethra 195 may not flow into the cavity being resected in the prostate lobe and for this reason fluid flow from the working end 140 can fill the space around the working end 140. In one variation, the pump mechanism 175 operates during the reciprocation cycle and saline will flow through channel 170 and outward from open termination 220 and outward from window 128 into the resected cavity, except for when the window 128 is closed. The saline thus irrigates the space around the working end 140 and supports the RF plasma formation about electrode 160A. In this method, the fluid flow volume through channel 170 can be set at any selected volume per cycle of reciprocation, for example from 0.5 cc to 10 cc's. This selected volume can be unrelated to an optional pulsed volume when the window 128 is closed. The volumes of fluid pumped can be adjusted by design of the volume of the pump chamber and piston stroke. In another embodiment, the probe shaft 110 could be configured with another flow channel to deliver fluid to the space in the prostate lobe 196 around the working end 140.

Still referring to the resection method of FIG. 10, the working end 140 also can be operated in another manner to cause coagulation. As described above, the resecting sleeve 120 can be stopped in a selected position within window 128 and optimal RF output and power can be delivered between electrodes 160A and 160B to heat fluid in the space around the working end 140 which will effectively coagulate tissue around the resected cavity. In such a coagulation mode, a foot pedal can be used to activate the system, and in on variation the foot pedal could be tapped to cause the coagulation mode to operate for a predetermined time interval, for example 10 seconds, 20 seconds, 20 seconds or 60 seconds. In another variation, the foot pedal could be depressed to actuate the coagulation mode until the pedal is released.

While the above embodiments have described a system that has a single motor 115 that operates both the resecting sleeve 120 and the pump mechanism 175, another variation could have a first motor in handle 108 that operates the resecting sleeve 120 and a second motor that actuates the pump mechanism 175. This option would allow the controller 150 to independently modulate parameters of both systems during each cycle of reciprocation and thus potentially allow for more modes of operation In the embodiment of FIGS. 1-3, the distal end of the probe has a fixed sharp tip 188. In another embodiment, a sharp tipped needle (not shown) could be extended and retracted from the distal body 186 by manipulation of an actuator portion in handle 108. In this variation, the needle tip would be extended only when the physician penetrated the working end through the urethra 195 (cf. FIG. 10). Thus, during the steps of resecting tissue in the prostate lobe under imaging, the dull tip of the probe would make it impossible or unlikely that the physician could inadvertently push the tip into the bladder 290 or through the prostate capsule wall.

In general, the tissue resecting device corresponding to the invention comprises a handle and elongated sleeve assembly comprising a windowed outer sleeve and an inner sleeve adapted to move relative to the window to resect tissue, and a motor in the handle configured to move the inner sleeve and operate a pump to provide a fluid flow through a channel in the sleeve assembly. In one variation, the tissue resecting has an inner resecting sleeve that is adapted to reciprocate relative to the window. In another embodiment, the resecting sleeve is adapted to rotate relative to the window. In another embodiment, the resecting sleeve is adapted to reciprocate and rotate relative to the window.

In another aspect of the invention, the pump mechanism 175 of FIGS. 1, 6A and 7A is a positive displacement pump and more specifically a piston pump. In other variations, the pump can be is selected from the group consisting of piston pumps, screw pumps, impeller pumps, peristaltic pumps, vane pumps, lobe pumps, plunger pumps and diaphragm pumps.

In another aspect of the invention, the resecting sleeve 120 comprises an electrode for electrosurgically resecting tissue. In another variation, the resecting sleeve can have a blade edge for cutting tissue.

In another aspect of the invention, the tissue resecting system includes a probe with an elongated sleeve assembly comprising a windowed outer sleeve and an inner sleeve adapted to move in a cycle to resect tissue interfacing with the window, and a pump mechanism in or proximate the handle configured to provide a fluid flow through a channel in the sleeve assembly. The pump mechanism can be adapted to provide the flow at a constant rate over each cycle of the inner sleeve, or the pump mechanism can be adapted to provide the flow at a non-constant rate over each cycle of the inner sleeve. In one variation, the pump is operated to provide a pulsed fluid flow.

In another aspect of the invention, the tissue resecting system includes a probe having an elongated outer sleeve with a closed distal end with a side-facing window that opens to an interior lumen in the sleeve, with an inner sleeve adapted to move longitudinally in the lumen between window open and window closed positions to thereby resect tissue in the window, and a resilient element disposed in distal end of the lumen adapted to interface with the distal end of the inner sleeve when in its distal-most position. In this variation, the system also includes a flow channel within the outer sleeve having an open termination in or proximate to the resilient element, wherein the resilient element is configured to contact the inner sleeve in its distal most position to seal the distal end of the passageway in the inner sleeve.

In another aspect of the invention, the tissue resecting system includes a probe having an elongated outer sleeve with a closed distal end and side-facing window that opens to an interior lumen, a motor driven inner sleeve adapted to reciprocate longitudinally in a first distal direction across the window to resect tissue and in a second proximal direction to thereby open the window wherein the inner sleeve carries an electrode for applying RF energy to tissue and wherein a controller moves the inner sleeve in the first direction at a first speed and moves the inner sleeve in the second direction at a second different speed. Different RF parameters can be used in the first and second directions.

Figure 11:
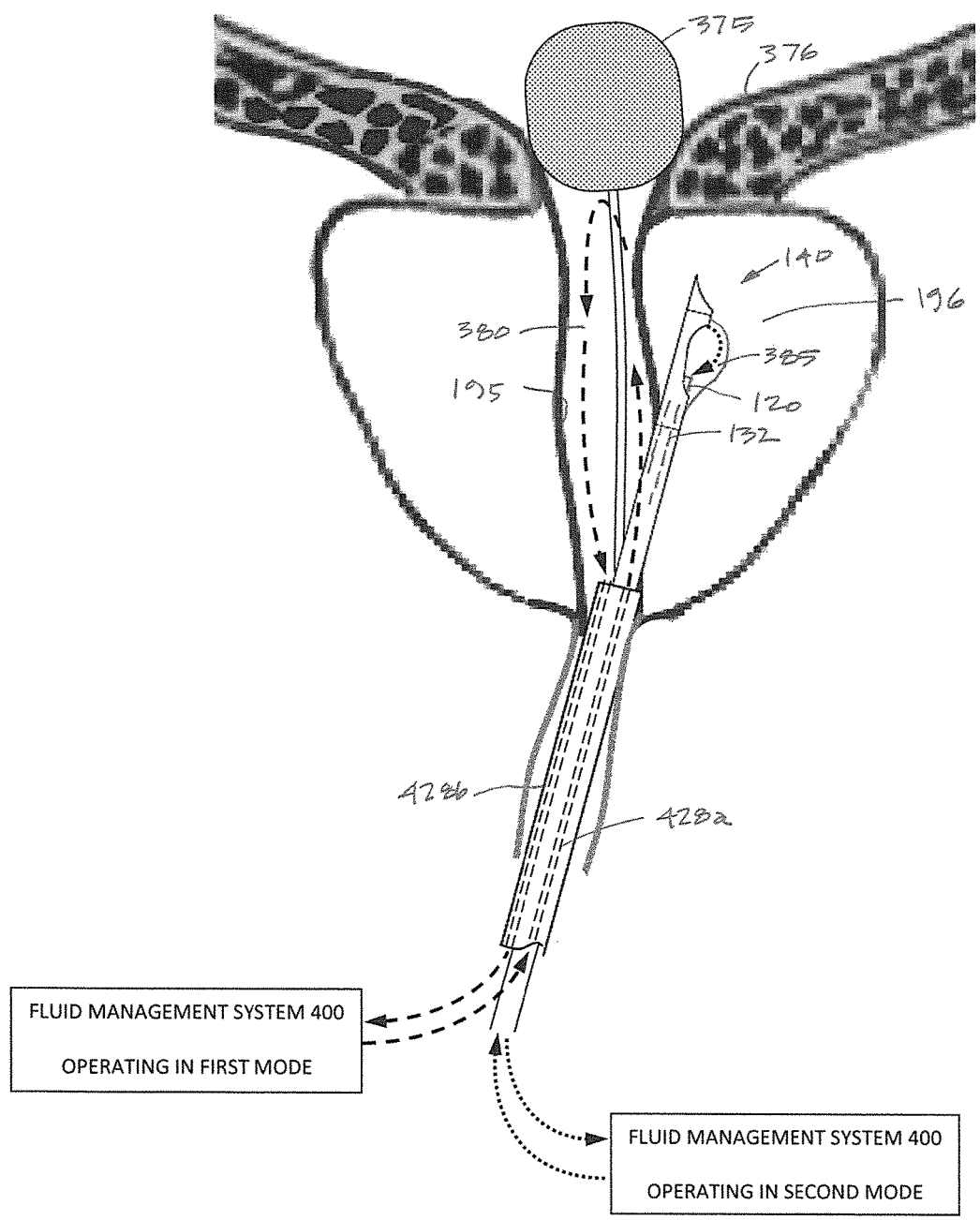
FIG. 11 is a representation of a method of fluid management with the device of FIG. 1 in an interstitial tissue resection procedure in a patient's prostate.
Figure 12A:
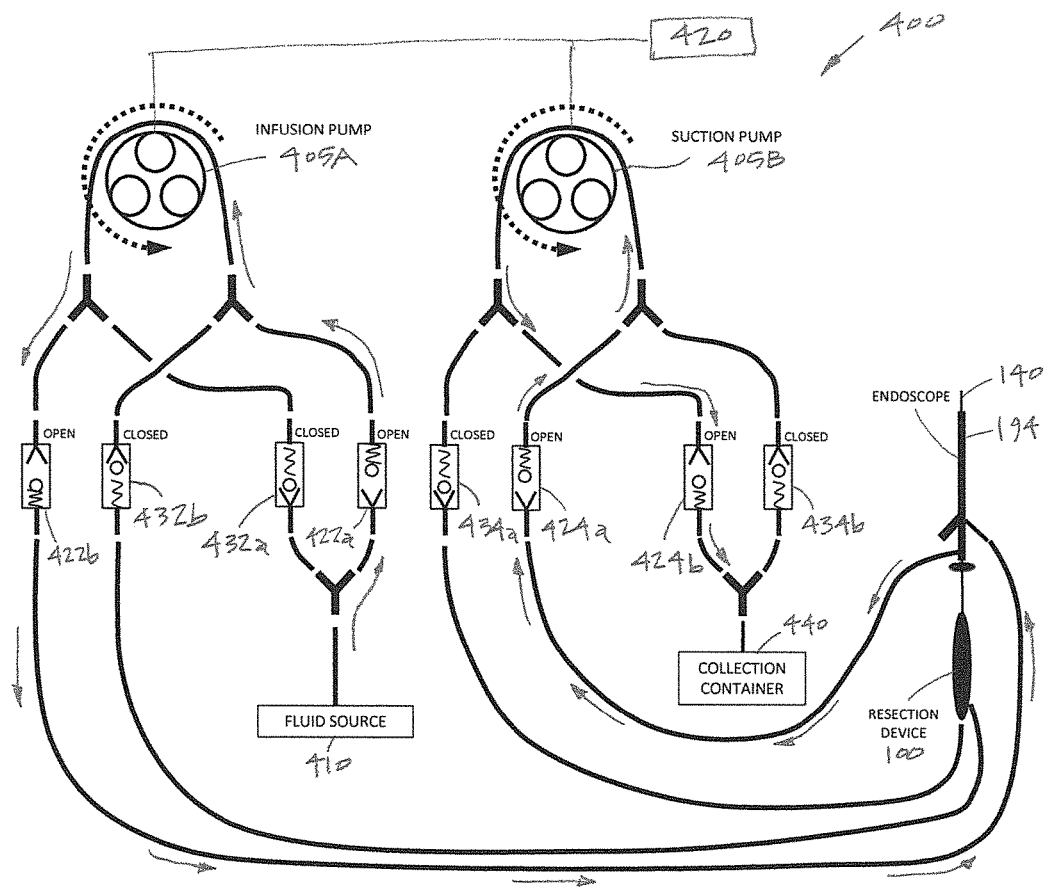
FIG. 12A is a diagram of a fluid management system employing bidirectional flow pumps for use with the device of FIG. 1 that is operating in a first mode to provide fluid flows to a first working space.
Figure 12B:
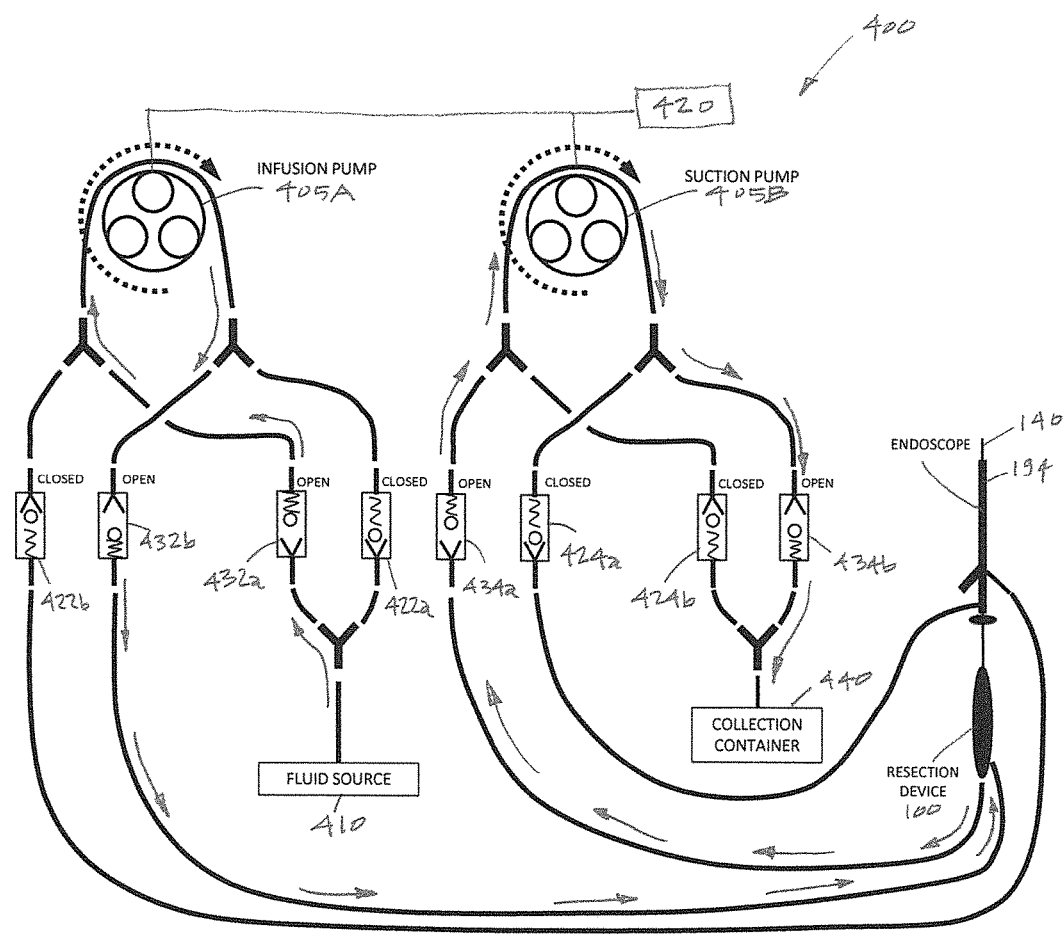
FIG. 12B is a diagram of the fluid management system of FIG. 12A that is operating in a second mode to provide fluid flows to a second working space.

FIGS. 11, 12A and 12B illustrate a fluid management system of the invention that is configured for use in the interstitial resection and extraction of tissue as shown in the method of FIG. 10. FIG. 11 depicts an interstitial resection method as in FIG. 10, except with further details on fluid management and fluid flows.

In FIG. 11, it can be seen that a Foley catheter with balloon 375 is in place in the bladder 376 which creates a working space 380 in the urethra 195 in which a controlled fluid pressure is required to maintain an open space to allow for endoscopic viewing. In FIG. 11, it can be further see that that the working end 140 of resecting device 105 is penetrated into the prostate lobe 196 and another transient working space 385 is created around the working end 140. As described above, during operation, the working end 140 requires a suitable inflow of saline to enable the plasma ablation and a suitable outflow to extract resected tissue slugs through the tissue-extraction channel 132 in resecting sleeve 120.

FIGS. 12A-12B are graphic representations of a fluid management system 400 that include two peristaltic pumps 405A and 405B as is known in the art, which is adapted to provide fluid flows to both working spaces 380 and 385 as shown in FIG. 11. A first pump or infusion pump 405A is adapted to provide controlled inflows from a single saline fluid source 410 to a targeted site, which in this case can be either site 380 in the urethra 195 or site 385 about the device working end 140 (FIG. 11). The system 400 has second pump or suction pump 405B for providing controlled outflows from a working space. The controller 420 within the system 400 then includes algorithms that modulate the pump speeds to maintain an operating parameter, such as fluid pressure in the working site or space. Other operating parameters such as inflow and outflow rates may be set within a range.

In order to simultaneously maintain a targeted operating parameter in two working spaces, two fluid management systems with a total of four pumps could be used.

FIGS. 11, 12A and 12B show a fluid management system 400 with only two pumps 405A and 405B but that is configured to operate in first and second modes to provide the functionality of four pumps, that is and infusion (inflow) and suction (outflow) pump for each working space 380 and 385 in FIG. 11. The system 400 and controller 420 provides the first and second operating modes by selectively operating both of the pumps in a first rotational directions or in a second opposing rotational directions. The two pumping operating modes are enabled by a series of one-way valves with branching or split tubing lines, e.g. lines having a single inlet connected by a Y-connector.

FIG. 12A illustrates the system operating in the first mode with the pumps operating in a first rotational direction (counter-clockwise when viewed from front). It can be seen that when the system is actuated, rotation of infusion pump 405A draws fluid from source 410 through open one-way valve 422a and pumps fluid through open valve 422b to flow through the flow channel 428a in the endoscope into space 380 (see FIG. 11). FIG. 12A further shows the rotation of suction pump 405B which draws fluid from the space 380 through flow channel 428b in the endoscope and through open one-way valve 424a and pumps fluid through open valve 424b into the collection container 440. While the pumps operate in this first direction, the other one-way valves 432a, 432b, 434a and 434b are maintained in the closed position by fluid pressures resulting from the pressure of the fluid flows.

FIG. 12B illustrates the system 400 operating in the second mode with the pumps operating in a second rotational direction (clockwise when viewed from front). When the fluid management system 400 is actuated in this mode, rotation of infusion pump 405A draws fluid from source 410 through open one-way valve 432a and pumps fluid through open valve 432b to flow to the inflow channel of the resection device 100 and through working end 140 to working space 385 (see FIG. 11). FIG. 12B further shows the clockwise rotation of suction pump 405B which draws fluid from space 385 through the extraction channel 132 of the resection device and through open one-way valve 434a and pumps fluid through open valve 434b into the collection container 440. While the pumps operate in this second (clockwise) direction, the other one-way valves 422a, 422b, 424a and 424b are maintained in the closed position by fluid pressures resulting from the fluid flows.

During operation, the controller 420 can use algorithms to automatically switch between the first and second modes. For example, the system can monitor a parameter in the first working space 380 (e.g., fluid pressure) with a pressure sensor system, and operate in the first mode to maintain the pressure within a pre-determined range. Typically, the pumps only operate intermittently to maintain a set pressure in space 380, so that there are time intervals in which the pumps may operate in the second mode.

During an interval of resecting tissue, the controller 420 can use algorithms to automatically switch to the second mode from the first mode when the resection device 100 is actuated and saline flows to the space 385 are needed.

As can be understood, the controller algorithms can provide for priorities as to whether the first or second mode is needed during any time interval based on feedback from operating parameters or site parameters. Typically, when the resection device 100 is resecting tissue, the controller would continuously provide at least some, e.g. at least a low volume of, saline flow to the working end in the prostate or other solid tissue which would take priority over flow to space 380 in the urethra or other body lumen or cavity. When, the resection device 100 is not activated, typically the first mode would have priority to provide a sufficient saline flow to maintain an open space in the urethra or other body lumen or cavity.

Figure 13A:
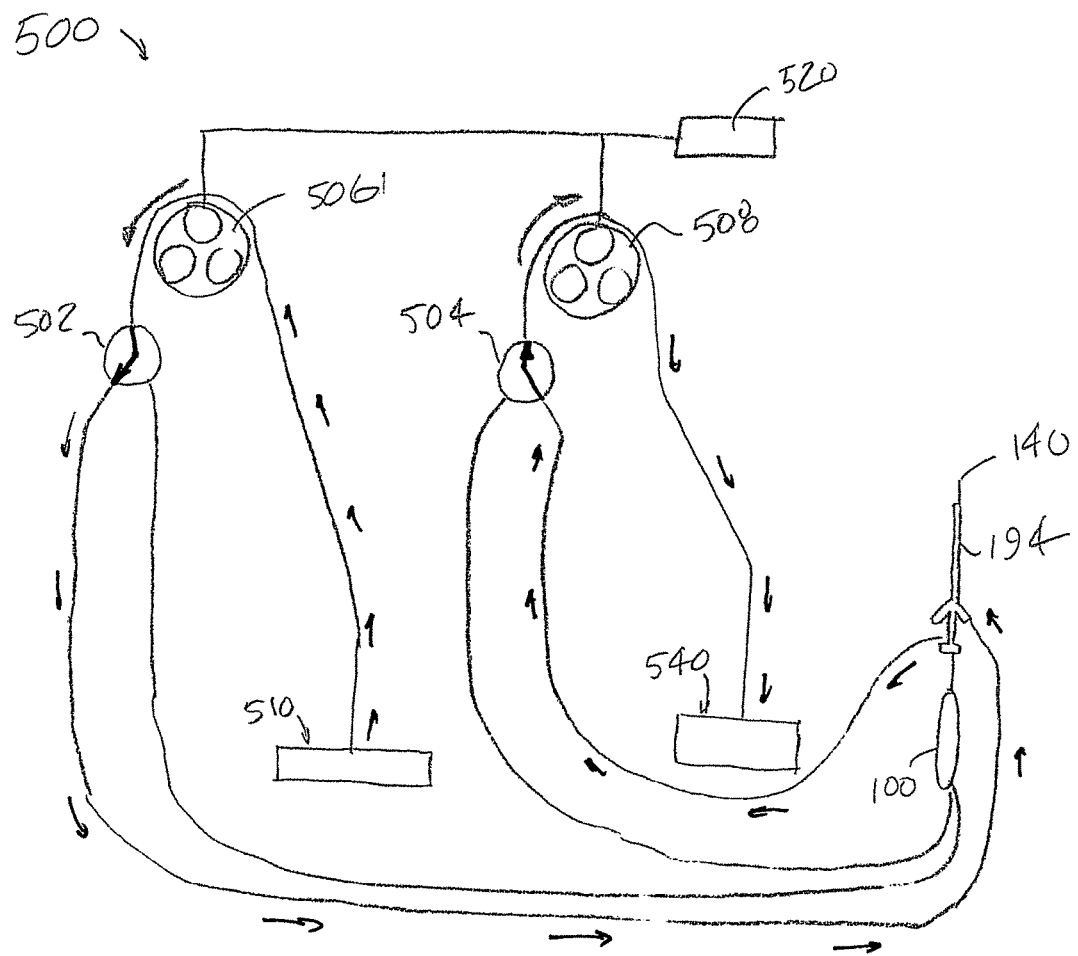
FIG. 13A is a diagram of an alternative embodiment of the fluid management system employing three-way valves for use with the device of FIG. 1 that is operating in a first mode to provide fluid flows to a first working space.

In another embodiment, as illustrated in FIGS. 13A and 13B, a system 500 uses powered three-way control valves 502 and 504, such as solenoid valves, controlled by controller 520 to direct fluid flow in either of the two paths shown in FIG. 11 with the pumps then only operating in one direction. Infusion control valve 502 can be placed in a first position, as shown in FIG. 13A, to direct saline or other infusate from source 510 through an infusion pump 506 to the resection device 100. Similarly. The aspiration control valve 504 can be positioned by the controller 520 to direct the outflow of fluid from the resection device 100 through outflow pump 508 to a collection continent 540.

When it is desired to redirect the infusate to the endoscope or cystoscope 194, the controller 510 can reposition the three-way control valve 506 to deliver the infusate to the endoscope and the three-way control valve 508 to collect the outflow of fluid from the endoscope or cystoscope 194, as illustrated in FIG. 13B. In contrast to the embodiment of FIGS. 12A and 12B, the direction of the pumps does not need to be changed Methods according to the present invention could utilize either of the one-way valve systems of FIGS. 12a and 12B or the powered on-off valve systems of FIGS. 13A and 13B.

What is claimed is:

1. A fluid management system configured to receive fluid from a fluid source, to deliver fluid to a medical probe having a first fluid infusion and aspiration circuit and a second fluid infusion and aspiration circuit, and to transfer fluid from the medical probe to a collection container, said system comprising:
- a first pump and valve assembly;
- a second pump and valve assembly; and
- a controller configured to operate the first pump and valve assembly to selectively provide fluid inflow from the fluid source to one of the first fluid infusion and aspiration circuit of the medical probe and the second fluid infusion and aspiration circuit of the medical probe and to operate the second pump and valve assembly to selectively transfer fluid outflow to the collection container from one of the first fluid infusion and aspiration circuit of the medical probe and the second fluid infusion and aspiration circuit of the medical probe;
- wherein the first pump and valve assembly includes a first pump which is operable to reverse flow direction and a first pair of one-way valves oriented to provide inflow to the first pump from the fluid source in both flow directions.

2. The fluid management system of claim 1, wherein of the second pump and valve assembly includes a second pump which is operable to reverse flow direction and a second pair of one-way valves oriented to provide outflow from the second pump to the first fluid infusion and aspiration circuit of the medical probe when the second pump is operated in a first flow direction and to provide outflow from the second pump to the second fluid infusion and aspiration circuit of the medical probe when the second pump is operated in a second flow direction.

3. The fluid management system of claim 2 wherein the first and second pumps are peristaltic pumps.

4. The fluid management system of claim 3 wherein the first and second pumps are operable in a first rotational direction to deliver fluid inflow and collect fluid outflow from the first fluid infusion and aspiration circuit of the medical probe.

5. The fluid management system of claim 4 wherein the first and second pumps are operable in a second rotational direction to deliver fluid inflow and collect fluid outflow from the second fluid infusion and aspiration circuit of the medical probe.

6. The fluid management system of claim 2 wherein the first and second pump and valve assemblies include tubing sets that carry the first and second valves.

7. The fluid management system of claim 6 wherein the first and second valves are one-way valves.

8. The fluid management system of claim 2 wherein the first and second pairs of one-way valves are adapted to direct fluid flows between the first and second flow paths in response to first and second flow directions established by the first and second pumps.

9. The fluid management system of claim 1 wherein the controller is further configured to maintain a fluid operating parameter delivered by the fluid management system within a pre-determined range.

10. The fluid management system of claim 9 wherein the fluid operating parameter consists of a first pump speed, a second pump speed, and a targeted pressure delivered to the first fluid infusion and aspiration circuit of the medical probe.

11. The fluid management system of claim 9 wherein the fluid operating parameter is established by a first pump speed, a second pump speed, and a targeted pressure delivered to the second fluid infusion and aspiration circuit of the medical probe.

12. A minimally invasive surgical system comprising:
- a fluid management system according to claim 1; and
- a viewing scope having a working channel and including the first fluid infusion and aspiration circuit.

13. The minimally invasive surgical system of claim 12 further comprising a surgical tool configured to be introduced through the working channel of the viewing scope and including the second fluid infusion and aspiration circuit.

14. A fluid management system configured to receive fluid from a fluid source, to deliver fluid to a medical probe having a first fluid infusion and aspiration circuit and a second fluid infusion and aspiration circuit, and to transfer fluid from the medical probe to a collection container, said system comprising:
- a first pump and valve assembly;
- a second pump and valve assembly; and
- a controller configured to operate the first pump and valve assembly to selectively provide fluid inflow from the fluid source to one of the first fluid infusion and aspiration circuit of the medical probe and the second fluid infusion and aspiration circuit of the medical probe and to operate the second pump and valve assembly to selectively transfer fluid outflow to the collection container from one of the first fluid infusion and aspiration circuit of the medical probe and the second fluid infusion and aspiration circuit of the medical probe;
- wherein the first and second pump and valve assemblies include first and second pumps that are operable in a single flow direction and first and second three-way valves that are selectively positionable by the controller (1) to deliver fluid inflow from the fluid source to one of either the first fluid infusion and aspiration circuit of the medical probe or the second fluid infusion and aspiration circuit of the medical probe and (2) to provide fluid outflow to the collection container from one of the first fluid infusion and aspiration circuit of the medical probe and the second fluid infusion and aspiration circuit of the medical probe.

15. The fluid management system of claim 14 wherein the controller is further configured to maintain a fluid operating parameter delivered by the fluid management system within a pre-determined range.

16. The fluid management system of claim 15 wherein the fluid operating parameter consists of a first pump speed, a second pump speed, and a targeted pressure delivered to the first fluid infusion and aspiration circuit of the medical probe.

17. The fluid management system of claim 15 wherein the fluid operating parameter is established by a first pump speed, a second pump speed, and a targeted pressure delivered to the second fluid infusion and aspiration circuit of the medical probe.

18. The fluid management system of claim 14 wherein the first and second pumps are peristaltic pumps.

19. The fluid management system of claim 18 wherein the first and second pumps are operable in a first rotational direction to deliver fluid inflow and collect fluid outflow from the first fluid infusion and aspiration circuit of the medical probe.

20. The fluid management system of claim 19 wherein the first and second pumps are operable in a second rotational direction to deliver fluid inflow and collect fluid outflow from the second fluid infusion and aspiration circuit of the medical probe.

21. The fluid management system of claim 14 wherein the first and second pump and valve assemblies include tubing sets that carry the first and second valves.

22. The fluid management system of claim 21 wherein the first and second valves are one-way valves.

23. A minimally invasive surgical system comprising:
a fluid management system according to claim 14; and
a viewing scope having a working channel and including the first fluid infusion and aspiration circuit.

24. The minimally invasive surgical system of claim 23 further comprising a surgical tool configured to be introduced through the working channel of the viewing scope and including the second fluid infusion and aspiration circuit.

* * * * *